United States Patent [19]
Paszczynski et al.

[11] Patent Number: 5,618,726
[45] Date of Patent: Apr. 8, 1997

[54] BIODEGRADABLE AZO DYES

[75] Inventors: Andrzej Paszczynski; Stefan Goszczynski; Ronald L. Crawford; Donald L. Crawford; Maria B. Pasti, all of Moscow, Id.

[73] Assignee: Idaho Research Foundation, Inc., Moscow, Id.

[21] Appl. No.: 345,261

[22] Filed: Nov. 23, 1994

Related U.S. Application Data

[63] Continuation of Ser. No. 970,716, Nov. 2, 1992, abandoned, which is a continuation-in-part of Ser. No. 930,162, Aug. 12, 1992, abandoned, which is a continuation-in-part of Ser. No. 615,514, Mar. 27, 1991, abandoned.

[51] Int. Cl.$^6$ ............... B09B 3/00; C12N 1/14; D06M 16/00
[52] U.S. Cl. ........... 435/262.5; 435/262; 435/254.1; 435/264
[58] Field of Search ............... 435/262.5, 255, 435/262, 254.1, 264

[56] References Cited

U.S. PATENT DOCUMENTS

| | | | |
|---|---|---|---|
| 313,118 | 3/1885 | Stebbins, Jr. | 262/262.5 |
| 2,788,344 | 4/1957 | Brassel | 435/262.5 |
| 3,297,679 | 1/1967 | Leuchs | 435/262.5 |
| 3,676,050 | 7/1972 | James | 262/262.5 |
| 3,905,952 | 9/1975 | Speck | 260/186 |
| 3,932,376 | 1/1976 | Feeman | 26/186 |
| 4,249,902 | 1/1981 | Kruchenberg et al. | 260/186 |
| 4,655,926 | 4/1987 | Chang et al. | 210/611 |
| 5,091,089 | 2/1992 | Shen et al. | 210/611 |
| 5,141,855 | 8/1992 | Schmittou | 435/262.5 |

FOREIGN PATENT DOCUMENTS

| | | |
|---|---|---|
| 2110614 | 3/1970 | Germany. |
| 48-75926 | 10/1973 | Japan. |
| 1562991 | 3/1980 | United Kingdom. |

OTHER PUBLICATIONS

"Interference of Aromatic Sulfo Groups in the Microbial Degradation of the Azo Dyes Orange I and Orange II,", Kulla et al *Arch. of Microbiol.*, 35:1–7 (1983).

"Biodegradation of Azo & Heterocylic Dyes by *Phanerochaete chrysosporium,*" *Applied and Environmental Microbiology*, Cripps et al, pp. 1114–1118, vol. 56, No. 4 (1990).

Kulla et al. "Experimental Evolution of Azo Dye–Degrading Bacteria," *Curr. Perspect. Microb. Ecol., Proc. Int. Symp. 3rd*, 663–667 (1984).

Haraguchi, "Degradation of Lignin–Related Polystyrene Derivatives by Soil Microflora and Micromonospora–SP Yb–1," *Lignin Biodegradation: Microbiology, Chemistry and Potential Applications*, CRC Press (vol. 2), 1980. pp. 123–126.

(List continued on next page.)

*Primary Examiner*—John Kight
*Assistant Examiner*—Louise Leary
*Attorney, Agent, or Firm*—Klarquist Sparkman Campbell Leigh & Whinston, LLP

[57] ABSTRACT

A composition comprises an azo dye having a lignin-like substitution pattern and an environmentally common microbe, such as Streptomyces or *Phanerochaete chrysosporium*. The composition may also comprise an azo dye having a lignin-like substitution pattern, an amount of lignin peroxidase effective to degrade the dye, and an amount of veratryl alcohol effective to recycle lignin peroxidase II to lignin peroxidase. The lignin peroxidase may be provided by an environmentally common microbe. Azo dyes substituted with lignin-like groups are completely mineralized by the environmentally common microbe. The biodegradable azo dye preferably includes a first aromatic ring having a first substituent R1 selected from hydroxy or lower alkoxy, a second substituent R2 selected from lower alkyl or lower alkoxy, and a third substituent R3 selected from lower alkoxy or halogen. In especially preferred embodiments the first substituent $R_1$ is hydroxy and is para to the azo group, and both $R_2$ and $R_3$ are electron-releasing substituents and are ortho to $R_1$.

27 Claims, 11 Drawing Sheets

OTHER PUBLICATIONS

Haraguchi, "Biodegradation of Lignin–Related Polystyrenes," *Lignin Biodegradation: Microbiology, Chemistry and Potential Applications*, CRC Press (vol. 2), 1980. pp. 147–159.

Brown, "Degradation of Dyestuffs: Part III—Investigations of the Ultimate Degradability," *Chemosphere*, vol. 16, No. 7, pp. 1539–1553 (1987).

Kulla, "Aerobic Bacterial Degradation of Azo Dyes," in *Microbiol Degradation of Xenobiotics and Recalcitrant Compounds*, Academic Press, London, pp. 387–399 (1981).

Brown, et al. "The Aerobic Biodegradability of Primary Aromatic Amines," *Chemosphere*, vol. 12, No. 3, pp. 405–414 (1983).

Rafii et al. "Azoreductase Activity of Anaerobic Bacteria Isolated from Human Intestinal Microflora," *Applied and Environmental Microbiology*, vol. 56, No. 7, pp. 2146–2151 (1990).

Mason, et al. "Inhibition of Azoreductase by Oxygen," *Molecular Pharmacology*, 14, pp. 665–671 (1978).

Ogawa, "Biodegradation of Azo Dyes in Multistage Rotating Biological Contractor Immobilized by Assimilating Bacteria," *Bull. Environ. Contam. Toxicol.*, 44:561–566 (1990).

Arjmand et al. "Mineralization of Chloraniline/Lignin Conjugates and of Free Chloroanailines by the White Rot Fungus *Phanerochaete chrysosporium*," *J. Agric. Food Chem.*, vol. 33, pp. 1055–1060 (1985).

Pasczcynski, "New Approach to Improve Degradation of Recalcitrant Azo Dyes by Streptomyces spp. and *Phanerochaete chrysosporium*," *Enzyme Microb, Technol.*, vol. 13, pp. 1–7 (1991).

Zimmerman, "Properties of Purified Orange II Axoreductase, the Enzyme Initiating Azo Dye Degradation by Pseudomonas KF46," *Eur. J. Biochem.* 129:197–203 (1982).

Wuhrman, "Investigation on Rate—Determining Factors in the Microbial Reduction of Azo Dyes," *European J. Appl. Microbiol. Biotechnol.* 9:325–338 (1980).

Haider, "Mineralization of 14C–Labelled Humic Acids and of Humic–Acid Bound 14C–Xenobiotics by *Phanerochaete Chrysosporium*," *Soil Biol. Biochem.* 20:425–429 (1988).

CAS Registry Handbook, pp. 1126R and 2766R (1974).

Colour Index, 3rd ed., vol. 4, pp. 4043 and 4087 (1971).

Index Chemicus, vol. 29, 95988 (1968). Goodman et al.

Aspro–Nicholas, Ltd., Chemical Abstracts, vol. 66, No. 75812n (1967).

Cappadona et al., Chemical Abstracts, vol. 86, No. 33764f (1977).

Gholse et al., Chemical Abstracts, vol. 90, No. 62022a (1979).

Jain et al., Chemical Abstracts, vol. 81, No. 38911h (1974).

Matusiak et al., "Chemical Abstracts", vol. 86, No. 21734b (1977).

Yoshida et al., I, *Chem. Lett.*, vol. 5, pp. 703–706 (1984).

Yoshida et al., II, *J. Phys. Chem.*, vol. 94, pp. 4254–4259 (1990).

*Degradation of Phenolic Compounds and Ring Cleavage of Catechol by Phanerochaete Chrysosporium*, Applied and Environmental Microbiology, vol. 46:191–197 (Jul., 1983). Leatham et al.

*Chemico–Biological Interactions in Biological Purification System II. Biodegradation of Azocompounds by Activated Sludge*, Bulletin of Environmental Contamination & Toxicology, vol. 17:214–218 (1977).Yoshikuni et al.

Notification of Transmittal of The International Search Report or the Declaration, PCT/US92/02345, first three pages, (Sep. 8, 1992).

Jacques, Chemical Abstracts, 96:198917C (1982).

Ribka, Angew. Chem., 70:241–4 (1958).

Silk et al., J. Chem. Soc., 3472–4 (1963).

Huyash et al. "Novel extracellular enzymes of *Phanerochaete chrysosporium*" *FEMS Microbiology Letters* 28 (1985) pp. 119–123.

Higson, F. Biosis 92:512767.

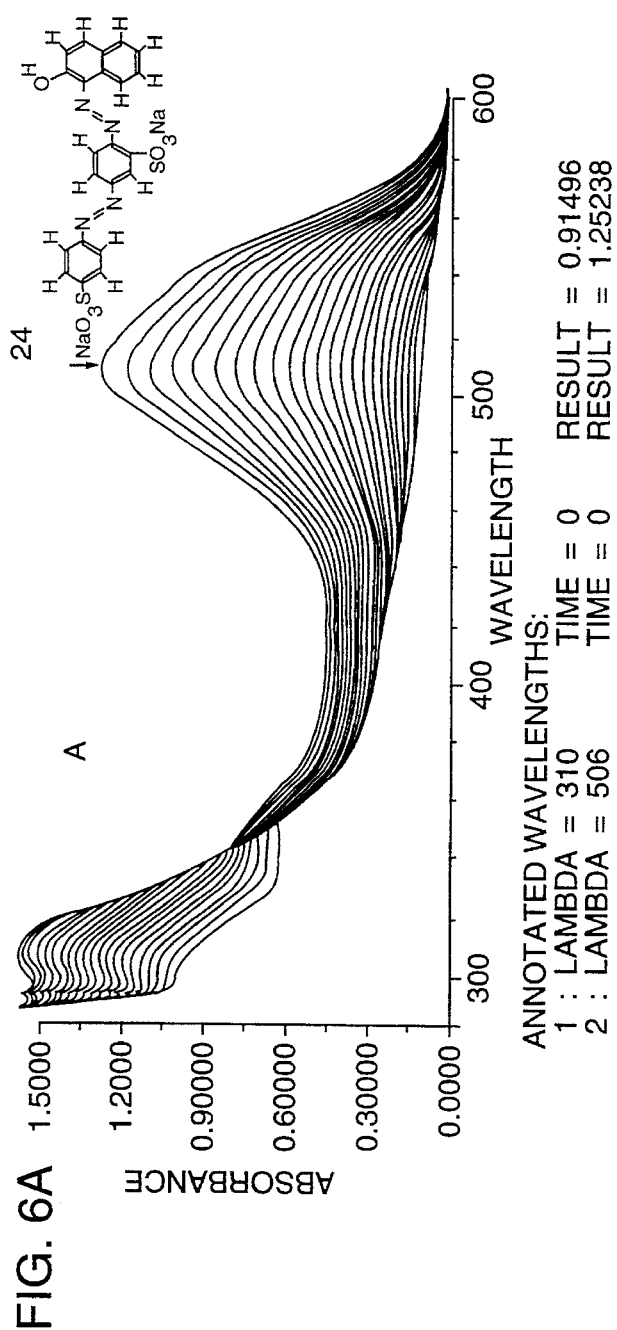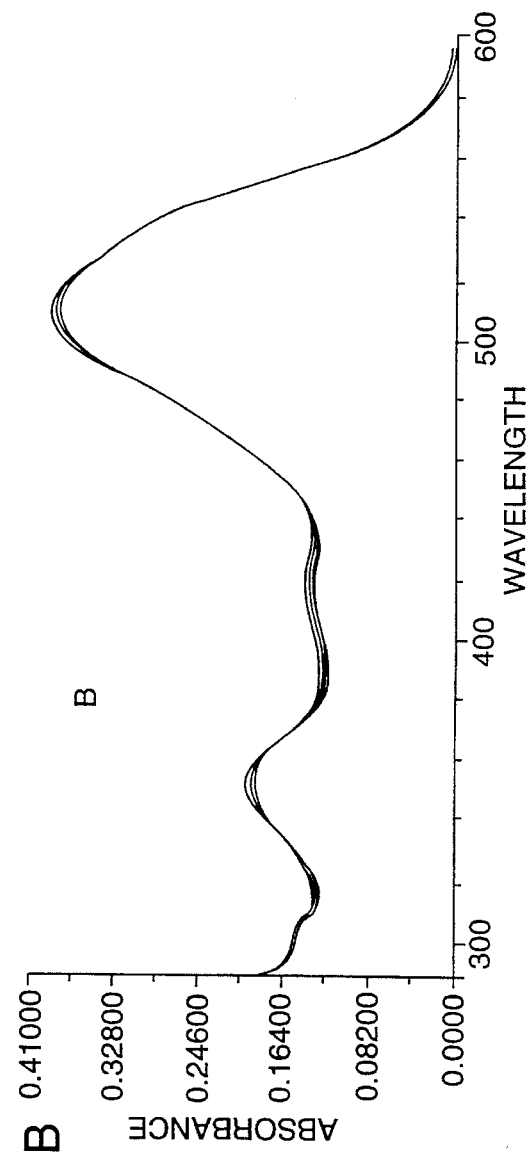
FIG. 6A
FIG. 6B

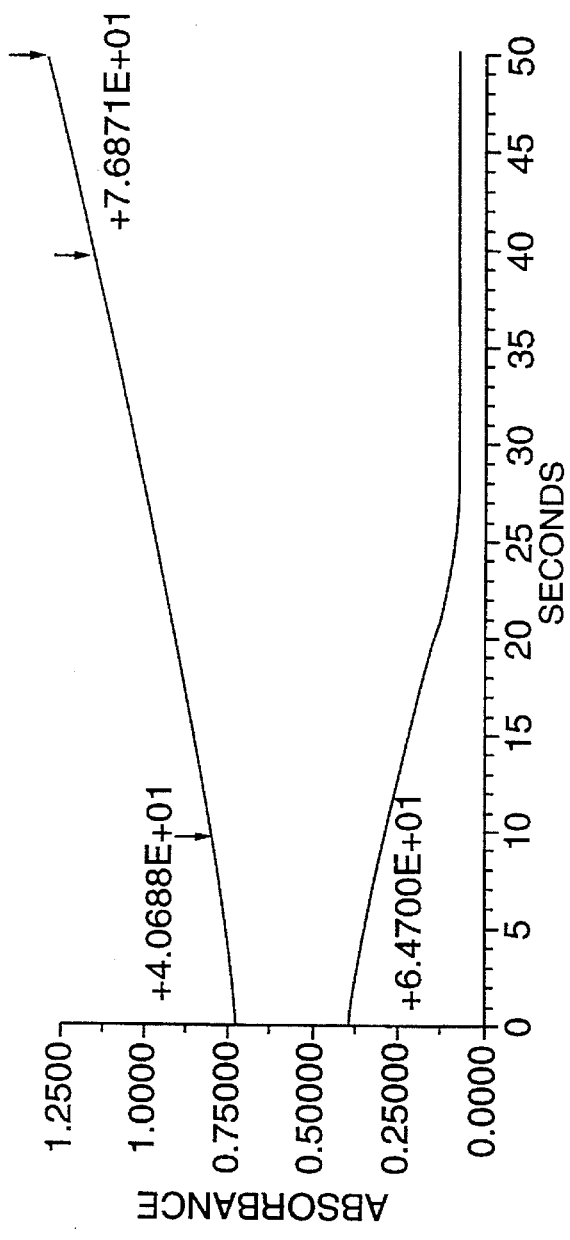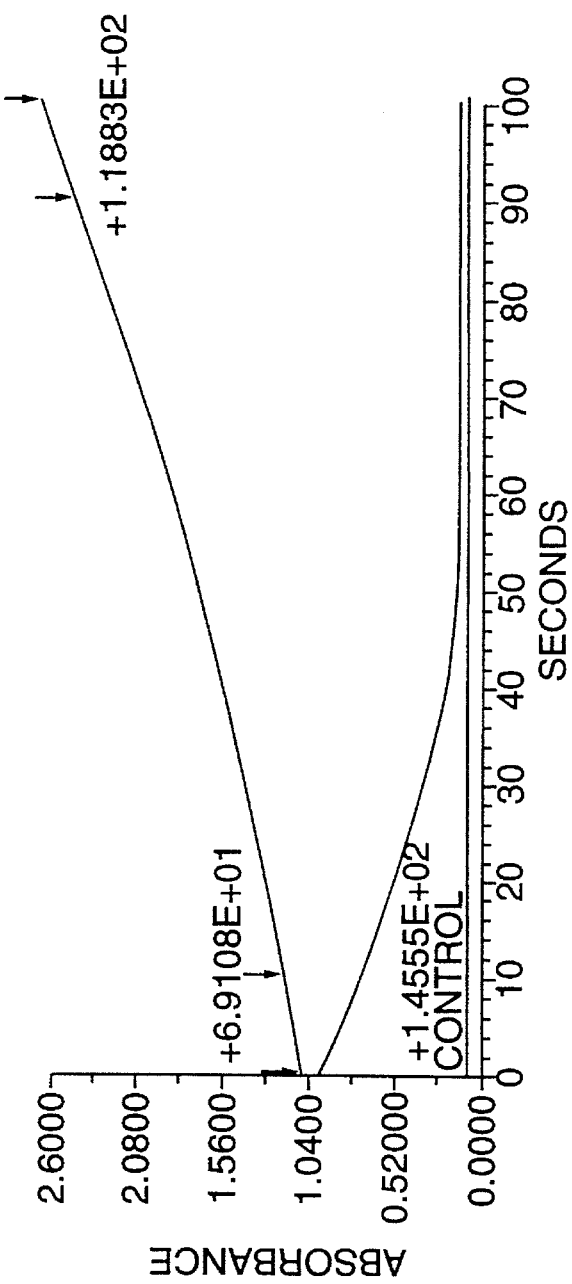
FIG. 8A
FIG. 8B

BIODEGRADABLE AZO DYES

GOVERNMENTAL SUPPORT

This research was supported in part by competitive Research grant 88-37233-4037 from the United States Department of Agriculture, and by grant BCS-8807000 from the National Science Foundation. The government may have certain rights in this invention.

CROSS REFERENCE TO RELATED APPLICATION

This application is a continuation of application Ser. No. 07/970,716, filed on Nov. 2, 1992, which is a continuation-in-part of prior application Ser. No. 07/930,162, filed on Aug. 12, 1992, which is a continuation-in-part of prior application Ser. No. 07/615,514, filed on Mar. 27, 1991, all now abandoned.

BACKGROUND OF THE INVENTION

1. Field of the Invention

This invention concerns a method of making xenobiotic compounds more biodegradable. More specifically, it concerns biodegradable azo dyes.

2. General Discussion of the Background

Azo dyes are important synthetic compounds that are widely used in the dyestuff and textile industries. Previously, persons skilled in the art believed that azo dyes are not biodegradable. Known azo dyes tend to persist in the environment unless subjected to costly physical and chemical decontamination processes. Compounds such as azo dyes which resist biodegradation are known as xenobiotics. The azo linkages or aromatic sulfo groups often found in these dyes are generally not synthesized by living organisms, which may help explain their recalcitrance to degradation. Detailed knowledge about biodegradation of these compounds in nature is limited.

Biologic waste treatment processes are sometimes more efficient and less expensive than physical-chemical waste treatment procedures, hence it would be desirable to provide a biological process using microorganisms that degrade xenobiotic azo dyes. Unfortunately, efforts to isolate such microorganisms have been largely unsuccessful in producing a commercially suitable process. Azo dye degrading Pseudomonas strains have been isolated from chemostat cultures by Kulla, "Aerobic bacterial degradation of azo dyes", in *Microbial Degradation of Xenobiotic and Recalcitrant Compounds*, Academic Press, Inc., London, 1981, pages 387–399 (1981). The degradation mechanism described for that Pseudomonas involved an oxygen-insensitive azoreductase which catalyzed the reductive cleavage of the azo group using NAD(P)H as an electron donor. Zimmerman, et al., *Eur. J. Biochem.*, 1982 129:197–203. Various anaerobic bacteria that degrade azo dyes have also been reported by Wuhrman, et al., *Eur. J. Appl. Microbiol-Biotechnol.*, 1980, 9:325–338 and Meyer, "Biodegradation of synthetic organic colorants", in *Microbial Degradation of Xenobiotic and Recalcitrant Compounds*, supra. However, under aerobic conditions these dyes have been considered to be essentially non-biodegradable.

Chang et al.'s U.S. Pat. No. 4,655,926 describes using the white rot fungi *Phanerochaete chrysosporium* to degrade effluent from a pulp or paper-making process. The effluent contains lignin or modified lignin. Furthermore, Cripps found that *Phanerochaete chrysosporium* aerobically degrades polycyclic hydrocarbons containing azo and sulfo groups. Cripps, et al., *Appl. Environ. Microbiol.*, 1990, 56:1114–1118. That paper described several unidentified metabolites of microbially degraded Tropaeolin O, Congo Red and Orange II after incubation with crude ligninase preparations, but the possible mechanism of degradation was not explained. Other investigators have shown that *P. chrysosporium* can mineralize chloroaniline/lignin conjugates and xenobiotic molecules bound to humic acids. Haider and Martin, *Soil Biol. Biochem.*, 1988, 20:425-249.

In spite of these advances, the degree of microbial degradation of many azo dyes has remained low. Kulla's azo dye degrading Pseudomonas is highly substrate specific, and requires extensive screening procedures to isolate biodegradative strains. The extreme specificity of Kulla's bacterial strains decreases their practical use in industry because industrial effluents contain mixtures of dyes. Kulla, et al., "Biodegradation of xenobiotics; experimental evolution of azo dye-degrading bacteria", in *Current Perspectives in Microbial Ecology*, (eds. M. J. Klug and C. A. Reddy), American Society for Microbiology, Washington, D.C., pages 663–667. Moreover, the Pseudomonal strains completely and irreversibly lose their biodegradative ability when grown with the specific substrate for ten generations, as disclosed at page 664 of that publication. Finally, sulfonated aromatic groups in the substrate dyes disturbed the microbial degradative pathways and limited the usefulness of these microorganisms in degrading the vast quantities of industrially produced azo dyes.

Accordingly, it is an object of this invention to provide azo dyes which are more completely biodegradable.

Another object of the invention is to provide such dyes which can be degraded more effectively and discarded less expensively than many previous azo dyes.

Yet another object of the invention is to provide such dyes which are less harmful to the environment.

Another object of this invention is to provide azo dyes which can be degraded by microorganisms with less substrate specificity.

Another object is to provide such dyes which are degraded by relatively common and genetically stable microorganisms that better retain their biodegradative capacity through successive generations.

Finally it is an object of the invention to provide an improved method of treating azo dyes in which sulfonated azo compounds can be degraded.

These and other objects of the invention will be understood more clearly by reference to the following detailed description.

SUMMARY OF THE INVENTION

A biodegradable dye compound is disclosed which contains an azo group having first and second nitrogen atoms linked to first and second aromatic rings. The first aromatic ring has a lignin-like substitution pattern that enhances biodegradability of the dye compound. The aromatic ring preferably has a substitution pattern that resembles a syringyl or guaiacyl moiety. In preferred embodiments, the ring has a first substituent $R_1$ selected from the group consisting of hydroxy, lower alkoxy, or amino. In other embodiments, the ring further includes a second substituent $R_2$ selected from the group consisting of hydrogen, alkyl, lower alkoxy and halogen. In yet other preferred embodiments, the ring includes a third substituent $R_3$ selected from the group consisting of lower alkyl, lower alkoxy and halogen. In especially preferred embodiments $R_1$ is para to the azo linkage. In other preferred embodiments $R_2$ is ortho to $R_1$. In especially preferred embodiments $R_1$ is para to the azo linkage and $R_2$ is ortho to $R_1$.

Especially preferred embodiments of the dye compound have a first substituent $R_1$ on the aromatic ring that is selected from the group consisting of hydroxy and lower alkoxy, a second substituent $R_2$ selected from the group consisting of lower alkyl and lower alkoxy, and a third substituent $R_3$ selected from the group consisting of lower alkoxy and halogen. With three substituents attached to the first aromatic ring, especially preferred embodiments have $R_1$ equal to hydroxy, with both $R_2$ and $R_3$ ortho to $R_1$. Especially preferred embodiments have $R_2$ and $R_3$ as a lower alkoxy, or $R_2$ lower alkyl and $R_3$ lower alkoxy. The biodegradable dye also may comprise a plurality of azo groups linked to first, second and third aromatic rings such that the compound is a fully conjugated system, with the first aromatic ring having a hydroxy and lower alkoxy group attached thereto.

These and other compounds can be included in a biodegradable composition in which azo dyes according to the present invention are combined with an environmentally common microbe capable of degrading the azo dye. A wide variety of microorganisms efficiently degrade these dyes, especially microorganisms in the soil microflora. Particularly useful are a wide variety of Streptomyces species and strains of specific Streptomyces species found in soil and elsewhere. Examples of two aerobic microorganisms which have been shown to degrade the dyes of the present invention are several soil Streptomyces species and the fungus *Phanerochaete chrysosporium*. When used in combination with Streptomyces, biodegradation is most enhanced in the disclosed embodiments when $R_1$ is a hydroxy group para to the azo linkage, particularly if $R_2$ is ortho to the hydroxy group, and more particularly if $R_2$ is ortho to the hydroxy group and is an electron-releasing group, such as lower alkyl or lower alkoxy.

Biodegradation with *Phanerochaete chrysosporium* is particularly enhanced in some embodiments wherein $R_1$ is hydroxy para to the azo linkage and $R_3$ is absent, especially if $R_2$ is a group that does not have a high degree of steric hindrance. Methyl, methoxy and halogen are examples of small groups with a low steric hindrance. The presence of $R_3$, however, can greatly enhance biodegradation in some embodiments wherein $R_1$ is a hydroxy group para to the azo linkage, and $R_2$ and $R_3$ are both ortho to $R_1$. Biodegradation is also enhanced if $R_2$ and/or $R_3$ are electron-releasing substituents such as lower alkyl or lower alkoxy. This enhanced biodegradation is observed with $R_3$ present even in embodiments wherein $R_1$ is not para to the azo linkage.

With compositions according to the present invention, azo dyes having lignin-like substitutions are converted to $CO_2$. Furthermore, commercially available azo dyes can be substituted with lignin-like substituents, such as guaiacol-like or syringyl-like functional groups, without interfering with the dye characteristics of the compound.

Compositions according to the present invention may also comprise azo dyes having lignin-like substitution patterns, an amount of lignin peroxidase effective to degrade the dye, and an amount of veratryl alcohol effective to recycle lignin peroxidase II to lignin peroxidase. Especially preferred compositions have lignin peroxidase provided by an environmentally common microbe, such as *Phanerochaete chrysosporium*.

Compositions according to the present invention may also comprise an azo dye and an amount of peroxidase effective to degrade the azo dye. The peroxidase may be manganese peroxidase and be provided by an environmentally common microbe such as *Phanerochaete chrysosporium*. Particularly suitable azo dyes for the composition have a hydroxy group para to the nitrogen atoms comprising the azo group. Even more suitable dyes are those that have one or two electron releasing substituents, such as lower alkyl or lower alkoxy groups, ortho to the hydroxy group.

In other embodiments of the invention, a preexisting azo dye can be modified after use but before disposal to render it more biodegradable by these organisms.

BRIEF DESCRIPTION OF THE DRAWINGS

FIGS. 6A shows the oxidation of veratryl alcohol and azo dye 24 by lignin peroxidase.

FIG. 6B shows the oxidation of azo dye 24 by lignin peroxidase in the absence of veratryl alcohol.

FIG. 8A shows the oxidation rate of veratryl alcohol and azo dye 24 by ligninase.

FIG. 8B shows the oxidation rate of veratryl alcohol and azo dye 28 by ligninase.

DETAILED DESCRIPTION OF PREFERRED EMBODIMENTS

I. OVERVIEW

Figure 1A:
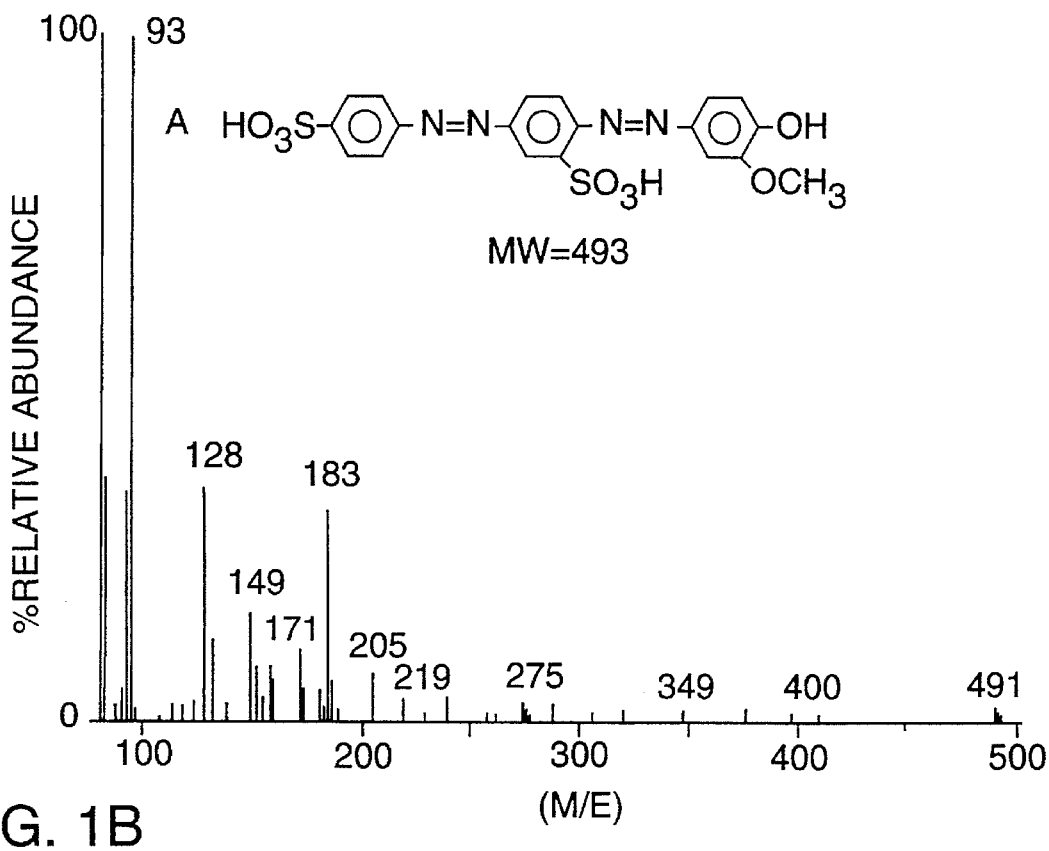
FIG. 1A shows the structure and MS spectra of the azo compound 4-(3-methoxy-4-hydroxyphenylazo)-azobenzene-3,4'-disulfonic acid of the present invention.

Three azo dyes were initially tested as substrates for degradation by twelve Streptomyces species and the white rot fungus *Phanerochaete chrysosporium*. The three azo dyes were the commercially available acid yellow 9 (4-amino-1,1'-azobenzene-3,4'-disulfonic acid), and two synthesized dyes. The two synthesized dyes were azo dye 1 [4-(3-methoxy-4-hydroxyphenylazo)-azobenzene-3,4'-disulfonic acid] and azo dye 2 (3-methoxy-4-hydroxy-azobenzene-4'-sulfonic acid). Sulfanilic acid and vanillic acid were also tested as substrates for degradation by the twelve Streptomyces species and the white-rot fungus *Phanerochaete chrysosporium*. None of the Streptomyces species degraded acid yellow 9 or sulfanilic acid. Linking a guaiacol molecule onto acid yellow 9 or sulfanilic acid via azo-linkages produced dyes that were decolorized by five of the twelve Streptomyces strains. These Streptomyces were those that could also attack vanillic acid, which has the same ring substitution pattern (4-hydroxy-3-methoxy) as guaiacol. While *P. chrysosporium* transformed both acid yellow 9 and sulfanilic acid, the two guaiacol-substituted azo dyes were decolorized more readily by *P. chrysosporium* than the corresponding unsubstituted molecules. Ligninase and manganese peroxidase preparations from the *P. chrysosporium* culture were apparently involved in the degradation.

Twenty-two azo dyes were then synthesized to further study the influence of substituents on azo dye biodegradability, and to explore the possibility of enhancing the biodegradability of azo dyes, without affecting their properties as dyes, by changing their chemical structures. Decolorization of monosulfonated mono azo dye derivatives of azobenzene by the Streptomyces spp. was observed with azo dyes 2–5 and 10. These dyes have the common structural pattern of a hydroxy group in the para position to the azo linkage, and at least one electron-releasing group, such as methoxy or one alkyl group, ortho to the hydroxy group. The fungus *P. chrysosporium* attacked Acid Yellow 9 to some extent and extensively decolorized azo dyes 1–4 and 9.

A different pattern was seen for three mono azo dye derivatives of naphthol. Streptomyces spp. decolorized 4-(4-hydroxy-naphthylazo)-benzenesulfonic acid (Orange I) but not 1-phenylazo-2-hydroxynaphthalinebenzene sulfonic acid (Acid Orange 12) or 4-(2-hydroxy-1-naphthylazo)benzenesulfonic acid (Orange II). *P. chrysosporium*, though able to transform these three azo dyes, decolorized Acid Orange 12 and Orange II more effectively than Orange I. A correlation was observed between the rate of decolorization of dyes by Streptomyces spp. and the rate of their oxidative cleavage by either a commercial preparation of horseradish peroxidase type II, extracellular peroxidase preparations of *S. chromofuscus* A11, or Mn(II)-peroxidase from *P. chrysosporium*. Ligninase of *P. chrysosporium* showed a dye specificity different from that of the other oxidative enzymes.

*P. chrysosporium* and Streptomyces spp. also mineralize (convert to $CO_2$) azo dyes having a lignin-like substitution pattern. Five $^{14}C$ radiolabeled azo dyes and sulfanilic acid were synthesized and, along with sulfanilic acid, were used to examine the relationship between dye substitution patterns and biodegradability (mineralization to $CO_2$). 4-Amino-[U-$^{14}C$]benzenesulfonic acid and 4-(3-sulfo-4-aminophenylazo)-[U-$^{14}C$]benzenesulfonic acid were used as representative compounds having sulfo groups or both sulfo and azo groups. Such compounds are not known to be present in the biosphere as natural products. Lignin-like fragments were introduced into the molecules of 4-amino-[U$^{14}C$]benzenesulfonic acid and 4-(3-sulfo-4-aminophenylazo)-[U-$^{14}C$]benzenesulfonic acid by coupling reactions with guaiacol (2-methoxyphenol) to produce azo dye 34, 4-(3-methoxy-4-hydroxyphenylazo)-[U-$^{14}C$]benzenesulfonic acid and azo dye 35, 4-(2-sulfo-3'-methoxy-4'-hydroxyazobenzene-4-azo)[U-$^{14}C$]benzenesulfonic acid, respectively. Azo dye 36, 4-(2-hydroxy-1-naphthylazo)-[U-$^{14}C$]benzenesulfonic acid, and azo dye 37, 4-(4-hydroxy-1-naphthylazo)-[U-$^{14}C$]benzenesulfonic acid, were synthesized and used to evaluate the ability of microorganisms to mineralize these commercially important compounds.

*Phanerochaete chrysosporium* effectively mineralized all of the sulfonated azo dyes. In contrast, *Streptomyces chromofuscus* was unable to mineralize aromatics with sulfo groups and both sulfo and azo groups. However, *S. chromofuscus* mediated the mineralization of modified dyes containing lignin-like fragments. Lignocellulolytic fungi and bacteria therefore can be used for the biodegradation of anionic azo dyes, which thus far have been considered to be among the xenobiotic compounds most resistant to biodegradation, if the dyes are modified to contain lignin-like fragments. Very specific structural changes in the azo dye molecules, i.e. changes that resemble lignin-like substitutions, enhanced their biodegradability.

II. MATERIALS

The following materials were purchased from Aldrich Chemical Company, Inc., 1001 West Saint Paul Avenue, Milwaukee, Wis.: sulfanilic acid, guaiacol, sodium nitrite, 4-hydroxy-3-methoxybenzoic acid (vanillic acid), phenol, substituted phenols, hydrochloric acid (37%, A.C.S. reagent grade), aniline, 1-napthol, 2-napthol, p-toluenesulfonyl chloride, 4-(4-dimethylaminophenylazo)benzenesulfonic acid (Methyl Orange 52, azo dye 14), 4-(4-diethylaminophenylazo)benzenesulfonic acid (Ethyl Orange, azo dye 15), 4-amino-1,1'-azobenzene-3,4'-disulfonic acid (Acid Yellow 9, azo dye 18), 1-phenylazo-2-hydroxynaphthalene-6-sulfonic acid (Acid Orange 12, azo dye 19), 2-methoxyethanol, Congo Red azo dye 20 (Direct Red No. 28) [international no. 573-58-01], Acid Red 114, azo dye 21 [6459-94-5], Direct blue 51, azo dye 22, Biebrich Scarlet, azo dye 24 [4196-99-0], Direct Blue 71, azo dye 25 [4399-55-7], Direct Red 75, azo dye 26 [2828-43-8], Chrysophenine, azo dye 27 [2870-32-8], Tartrazine, azo dye 28 [1934-21-0], Direct Yellow 27, azo dye 29, and veratryl alcohol. All chemicals were reagent or HPLC grade, unless specified otherwise, and were used as purchased.

Azo dye 4-amino-1,1'-azobenzene-3,4'-disulfonic acid (acid yellow 9), 4-aminoantipyrine, 2,4-dichlorophenol,

[U-$^{14}$C]Aniline-hemisulfate and 2,2'-dimethylsuccinic acid were purchased from Sigma Chemical Co.

III. SYNTHESIS OF AZO DYES

Azo dyes 1 and 2 were synthesized by attaching guaiacol through an azo linkage to acid yellow 9, forming 4-(3-methoxy-4-hydroxyphenylazo)-azobenzene-3,4'-disulfonic acid (azo dye 1), or to sulfanilic acid, forming 3-methoxy-4-hydroxy-azobenzene-4'-sulfonic acid (azo dye 2). Vanillylacetone was synthesized as taught by Huynh and Crawford, "Novel Extracellular Enzymes (Ligninases) of *Phanerochaete chrysosporium*," *FEMS Microbiol. Lett.*, 28:119–123, 1985.

A. Synthesis of Azo Dye 1

Azo dye 1 [4-(3-methoxy-4-hydroxyphenylazo)-azobenzene-3,4'-disulfonic acid] was synthesized by dissolving the sodium salt of 4-Amino-1,1'-azobenzene-3,4'-disulfonic acid (Yellow 9) (0.76 g) in 5% sodium hydroxide (8 ml). A solution of sodium nitrite (0.14 g in 0.5 ml of water) was added to this mixture. Crushed ice (10 g) and concentrated HCl (1.8 ml) was introduced to the solution, which was then vigorously stirred for 15 minutes, thereby forming diazotised Yellow 9. A cooled guaiacol (2-methoxyphenol) solution was formed (0.25 g dissolved in 3.2 ml 5% sodium hydroxide) and the diazotised yellow 9 solution was added to the guaiacol solution portionwise over 15 minutes with mechanical stirring. Saturated sodium chloride solution was added (15 ml), and the mixture was left to crystallize overnight at 5° C. The crystalline product was filtered, washed with acetone and ether, and dried in air. Dark brown crystals (0.98 g) were collected. (86.6% of theoretical yield).

B. Synthesis of Azo Dye 2

Azo dye 2 [3-methoxy-4-hydroxy-azobenzene-4'-sulfonic acid] was synthesized by suspending sulfanilic acid [4-amino sulfonic acid] (1.73 g) in 23 ml of water. To this suspension was added 8 ml of 5% NaOH. The mixture was stirred until the acid dissolved and then sodium nitrite solution (0.7 g in 2 ml H$_2$O) was added. Diazotised sulfanilic acid was formed by pouring the solution with mixing onto a crushed ice (25 g) and concentrated HCl (2 ml) mixture until copious precipitation took place (KJ starch test was positive). The diazotized sulfanilic acid was added portionwise to a cooled guaiacol solution (1.24 g in 20 ml 5% sodium hydroxide) with stirring. NaCl (20 g) was added and stirring was continued for 30 minutes at room temperature. The crystalline deep-orange precipitate was filtered off and washed with ethanol and ether; 2.62 g of the product was obtained (64.4% of theoretical yield).

C. Synthesis of Azo Dyes 3–15, 18–19

Azo dyes 3–13 were synthesized as follows. Sulfanilic acid (3.8 g, 22 mmol) was dissolved in 1N sodium hydroxide solution (22 ml, 22 mmol), and 5N sodium nitrite solution (4.4 ml, 22 mmol) was added. Concentrated hydrochloric acid (4 ml, 46 mmol) was poured on crushed ice (20 g) and the solution of sodium sulfanilate and sodium nitrite was introduced to the hydrochloric acid-crushed ice mixture with mechanical stirring over a 3-min period. The reaction mixture was kept for 2 min in an ice-water bath, and the white crystalline precipitate was then filtered off and washed with three (5 ml) portions of cold water. To avoid the possibility of explosion, the crystalline precipitate, a diazonium betaine, was kept wet and no pressure was applied to the filter cake. The wet material was transferred to water (20 ml), and the suspension kept at 0° C. for the next reaction step.

Phenol (20 mmol), or a substituted phenol (20 mmol) having the substitution pattern of the desired azo dye, was dissolved in 1N sodium hydroxide solution (20 ml, 20 mmol), and the solution was stirred vigorously while cooled in a salt-ice bath. If sodium phenolate precipitated out, water was added to keep the solution homogeneous. The cooled (0° C. to 5° C.) phenolate solution was stirred mechanically in a salt-ice bath, and the suspension of diazonium betaine was added in small portions over a 10-min period to couple the phenol and diazonium betaine. The coupling product precipitated immediately or after a brief interval. The thick crystalline reaction mixture was stirred for 3 h at 0° C. and then left overnight at 4° C.

To dissolve the crystals the reaction mixture was warmed in a water bath at 60° C. for 3 h. If solubilization was incomplete under these conditions, the temperature was increased to 90° C. and, if necessary, more water was added. The homogeneous solution was refrigerated overnight for slow crystallization. The deposited crystals were filtered off and washed three times with 2 ml of cold water. The crystals were air-dried in a desiccator over anhydrous calcium chloride, or in a vacuum oven. The yield of sodium salt was 14–16 mmol (70–80%) when phenol with the free para position was used as a substrate. Additional azo dye could be recovered by acidifying the filtrate with concentrated hydrochloric acid (5 ml, 60 mmol). The crystals were filtered off, washed with water and ethanol, and dried. Usually 2–4 mmol of high-purity azo dye was recovered (10–20%) as free acid. When para-substituted phenol was used the yield of sodium salt was about 10 mmol (50%) and no further recovery by acidification was possible.

D. Synthesis of Azo Dyes 16 and 17

Azo dyes 16 and 17 were synthesized by first coupling phenol or guaiacol with the diazonium betaine as above. The azo dye precursor (10 mmol) was then dissolved in 2N sodium hydroxide solution (15 ml, 30 mmol) and treated with dimethyl sulfate (3 ml, 30 ml). This procedure methylated the hydroxy group to produce azo dye 16 and azo dye 17.

E. Synthesis of Azo Dye 20

Azo dye 20 was prepared as described by Schündehütte's "Methoden Zur Herstellung und Umwandlung von Diarylazoverbindungen," p. 236 of *Methoden der Organischen Chemie*, vol. X/3 (1965). Accordingly, diazotised sulfanilic acid was coupled with p-toluenesulfonanilide, followed by hydrolysis. The crude product was purified by recrystallization of the sodium salt from a water-ethanol solution, followed by precipitation by acidifying the filtrate with concentrated hydrochloric acid.

F. Synthesis of Azo Dyes 21 and 22

Coupling procedures were completed as described for the preparation of amino-naphthols in *Organic Synthesis*, Coll. Vol. 2:33–42. The resulting compounds were purified by recrystallization from a water-ethanol acid.

G. Synthesis of $^{14}$C-Labeled Azo Dyes 33–37

[U-$^{14}$C]Sulfanilic acid. [U-$^{14}$C]aniline (0.93 g, 10 mmol, 25 µCi/mmol) was sulfonated as described elsewhere ("Vogel's Textbook of Practical Organic Chemistry," p. 912, 5th Ed., Longman Scientific & Technical Pub., John Wiley & Sons, New York(1989)), except that the product was not recrystallized. The crude product was dissolved in 1% sodium hydroxide solution, treated with decolorizing carbon, filtered, and precipitated with dilute hydrochloric acid. The product was colorless crystals (1.40 g, 8.1 mmol); specific activity, $3.2 \times 10^5$ dpm/mg; yield, 81%.

4-Sulfobenzene diazonium betaine. [U-$^{14}$C]Sulfanilic acid (0.17 g, 1 mmol, 25 µCi) was diazotized under standard conditions (Vogel, Id., p. 951) and the crystalline suspension was used immediately in a coupling reaction.

Azo Dye 34

[4-(3-Methoxy-4-hydroxyphenylazo-[U-$^{14}$C]benzenesulfonic acid]

4-Sulfobenzenediazonium betaine (prepared from 1 mmol of [U-$^{14}$C]sulfanilic acid, $3.2 \times 10^5$ dpm/mg) was coupled with guaiacol according to a procedure given elsewhere (Jacobs et al., *J. Am. Chem. Soc.*, 41:458–474). The product was metallic green needles (mono- hydrate; 0.30 g, 0.92 mmol, 23 µCi); specific activity, $1.7 \times 10^5$ dmp/mg; yield, 92%.

Azo Dye 37

4-(4-Hydroxynaphthylazo)-[U-$^{14}$C]Benzenesulfonic Acid 1-naphthol (0.15 g, 1.05 mmol) was coupled with 4-sulfobenzenediazonium betaine, prepared from 1 mmol of sulfanilic acid, in an ethanol-water solution according to the procedure of Slotta et al., "Zur Konstitution der Azo-Indikatoren. I Mitteilung: α-Napthol-Orange," *Chem. Ber.* 68:86–94). The crude product (0.29 g, 88%) was purified by recrystallization from water and an ethanol-acetone mixture. The product was black-purple needles (0.20 g, 0.61 mmol, 15.2 µCi); specific activity, $1.7 \times 10^5$ dpm/mg; yield, 61%.

Azo Dye 36

4-(2-Hydroxynaphthylazo)-[U-$^{14}$C]Benzenesulfonic Acid Sodium Salt 2-naphthol (0.15 g, 1.05 mmol) was coupled in an alkaline medium with a water suspension of 4-sulfobenzenediazonium betaine prepared from 1.0 mmol of [U-$^{14}$C]sulfanilic acid (Vogel, Id., at p. 950). The product was orange leaflets (dihydrate; 0.30 g, 0.78 mmol, 19.3 µCi); specific activity, $1.4 \times 10^5$ dpm/mg; yield, 78%.

p-Toluenesulfonanilide. Aniline (5 g, 54 mmol) was reacted with p-toluenesulfochloride (15 g, 78 mmol) in 10% sodium hydroxide solution under standard conditions (Vogel, Id, at p. 1275). The product (8.9 g, 36 mmol) was twice recrystallized from ethanol; the melting point was 102°–103° C., yield, 67%.

4-[4-(p-Tolylsulfamino)phenylazo]-[U-$^{14}$C]benezenesulfonic acid sodium salt. p-Toluenesulfonanilide (0.5 g, 2 mmol) was dissolved in 5% sodium hydroxide (1.6 ml, 2.1 mmol), ice (3 g) was added, and a suspension of p-sulfobenzenediazonium betaine (prepared from 2.0 mmol of [U-$^{14}$C] sulfanilic acid) was added over a period of 5 min while the reaction mixture was mechanically stirred in a salt-ice bath. After 4 hours, the yellow crystalline reaction mixture was filtered off, and the product was washed on the filter with ice-cold water and air-dried. The crude product (0.75 g; yield, 83%) was taken to the next step.

4-(4-Aminophenylazo)-[U-$^{14}$C]benzenesulfonic acid. 4-[4-(p-Tolylsulfamino)phenylazo]-[U-$^{14}$C]benzenesulfonic acid (0.75 g, 1.6 mmol, 40 µCi) was dissolved in 90% sulfuric acid (2 ml, 3.6 g, 33 mmol), warmed to 40° C., and kept at this temperature for 4 h. The reaction mixture was poured onto ice, and the precipitated product was filtered, washed with water, and dried at room temperature. The product was cherry-red crystals (0.34 g, 1.2 mmol, 30 µCi).

Azo Dye 33

4-(3-Sulfo-4-Aminophenylazo)-[U-$^{14}$C]Benzenesulfonic Acid 4-(4-Aminophenylazo)-[U-$^{14}$C]benzenesulfonic acid (0.34 g, 1.2 mmol, 30 µCi) was dissolved in fuming (20% $SO_3$) sulfuric acid (1.0 ml, 1.93 g, 20.6 mmol), warmed to 60° C., and kept at this temperature for 7 hours. After cooling to room temperature, the reaction mixture was treated with crushed ice (5 g) and the precipitated product, was filtered off. The crude product was dissolved in 5% sodium hydrogen carbonate (2–2.5 ml) to reach pH-4, and a small amount of undissolved solid material was filtered off and discarded. The filtrate was treated with concentrated hydrochloric acid (10 ml) and the purified product, 4-(3-Sulfo-4-aminophenylazo)-[U-$^{14}$C]benzenesulfonic acid, was filtered and washed with ethanol and ether. The product was metallic glittering dark-purple needles (0.32 g, 0.90 mmol, 22.5 µCi); specific activity, $1.6 \times 10^5$ dpm/mg; yield, 75%.

Azo Dye 35

4-(2-Sulfo-3'-Methoxy-4'-Hydroxyazobenzene-4-Azo)-[U-$^{14}$C]Benzenesulfonic Acid Monosodium Salt 4-(3-Sulfo-4-aminophenylazo)-[U-$^{14}$C]benzenesulfonic acid (0.18 g, 0.5 mmol, 12.5 µCi) was dissolved in 2% sodium hydroxide solution (2 ml). 1N sodium nitrite solution (0.5 ml, 0.5 mmol) was added, and the mixture was poured onto ice (3 g) and treated with concentrated HCl (0.2 ml). The thick crystalline suspension was kept in an ice-water bath, with occasional mixing, for 15 min. Guaiacol (65 mg, 0.52 mmol) was dissolved in 2% sodium hydroxide solution (1 ml) and diazonium salt suspension was added portion wise over 10 minutes while the reaction mixture was mechanically stirred in a salt-ice bath. The thick crystalline paste was kept at 0° C. for 3 hours. The reaction product was filtered off, washed with acetone, and dried. The product, 4-(2-Sulfo-3'-methoxy-4'-hydroxyazobenzene-4-azo)-[U-$^{14}$C]benzenesulfonic acid monosodium salt, was yellow crystals (0.185 g, 0.36 mmol, 9.0 µCi); specific activity, $1.1 \times 10^5$ dpm/mg; yield, 72%.

$^{14}$C-labeled dyes were all of 99% or greater radiochemical purity as determined by HPLC and/or TLC coupled with the counting of the radioactivity associated with dye peaks and/or spots.

Azo Dye 1
4-(3-methoxy-4-hydroxyphenylazo)-azobenzene-3,4'-disulfonic acid
(as supported by the MS spectra shown in FIG. 1A)

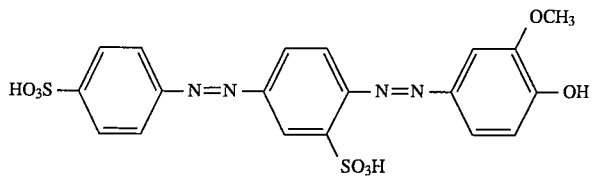

Figure 1B:
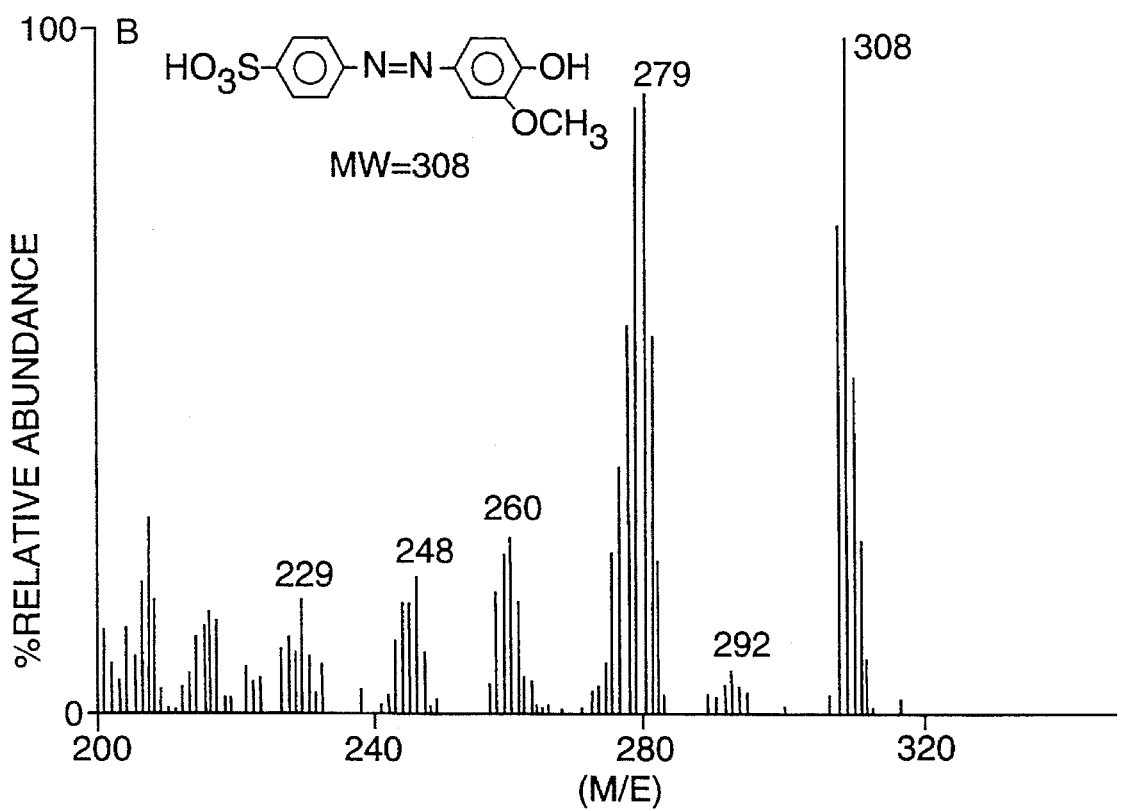
FIG. 1B shows the structure and MS spectra of the azo compound 3-methoxy-4-hydroxy-azobenzene-4'-sulfonic acid of the present invention.

Azo Dye 2
3-methoxy-4-hydroxy-azobenzene-4'-sulfonic acid
(as supported by the MS spectra shown in FIG. 1B)

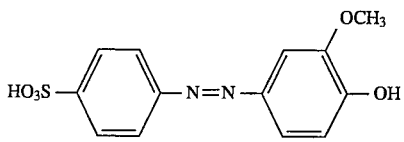

Azo Dye 3
3,5-dimethyl-4-hydroxy-azobenzene-4'-sulfonic acid

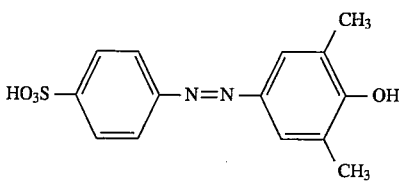

Azo Dye 4
3,5-dimethoxy-4-hydroxy-azobenzene-4'-sulfonic acid

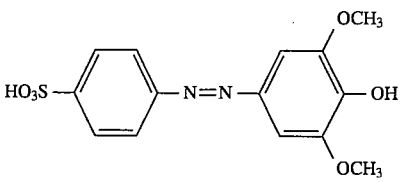

Azo Dye 5
3-methyl-4-hydroxy-azobenzene-4'-sulfonic acid

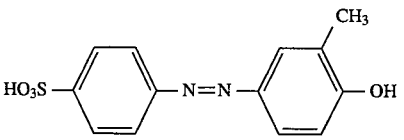

Azo Dye 6
4-hydroxy-azobenzene-4'-sulfonic acid

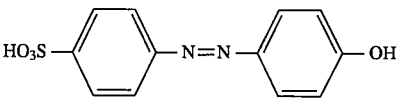

Azo Dye 7
2-hydroxy-4,5-dimethyl-azobenzene-4'-sulfonic acid

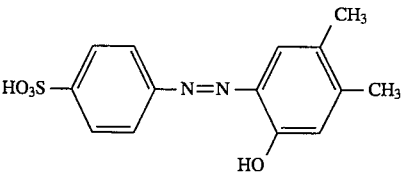

-continued

Azo Dye 8
2-hydroxy-5-methyl-azobenzene-4'-sulfonic acid

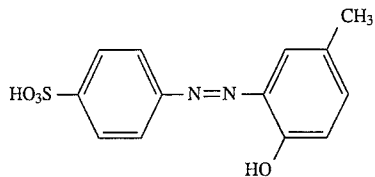

Azo Dye 9
2-hydroxy-5-ethyl-azobenzene-4'-sulfonic acid

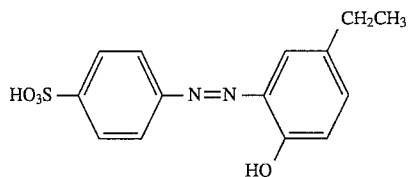

Azo Dye 10
3-sec-butyl-4-hydroxy-azobenzene-4'-sulfonic acid

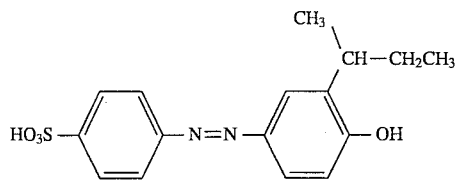

Azo Dye 11
2-hydroxy-3-methoxy-5-methyl-azobenzene-4'-sulfonic acid

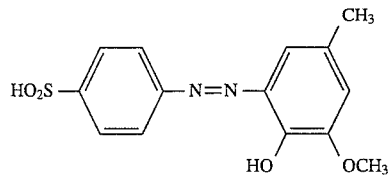

Azo Dye 12
3,5-difluoro-4-hydroxy-azobenzene-4'-sulfonic acid

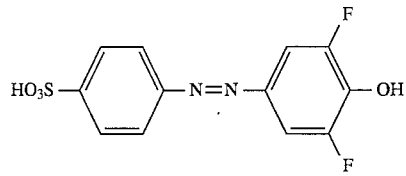

Azo Dye 13
3-chloro-4-hydroxy-azobenzene-4'-sulfonic acid

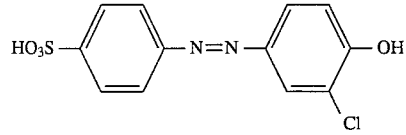

Azo Dye 14
4-dimethylamino-azobenzene-4'-sulfonic acid

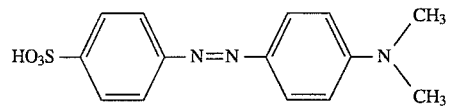

-continued
Azo Dye 15
4-diethylamino-azobenzene-4'-sulfonic acid
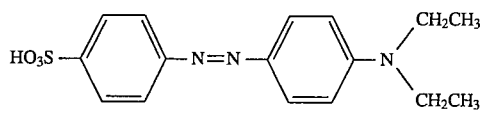
Azo Dye 16
4-methoxy-azobenzene-4'-sulfonic acid
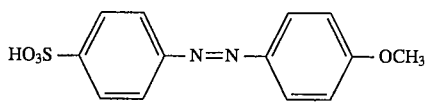
Azo Dye 17
3,4-dimethoxy-azobenzene-4'-sulfonic acid
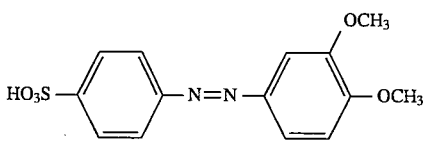
Azo Dye 18
4-amino-1,1'-azobenzene-3,4'-disulfonic acid
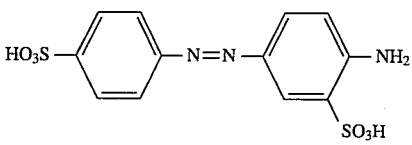
Azo Dye 19
1-phenylazo-2-hydroxynapthalene-6-sulfonic acid, Crocein Orange, G, C.I. 15970
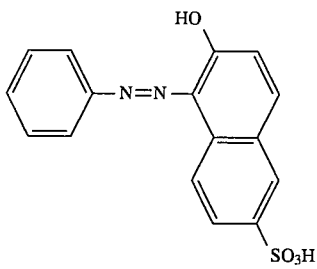
Azo Dye 20
Sodium diphenyl bis-alpha-napthaleneamine sulfonate, Congo Red, C.I. 22120
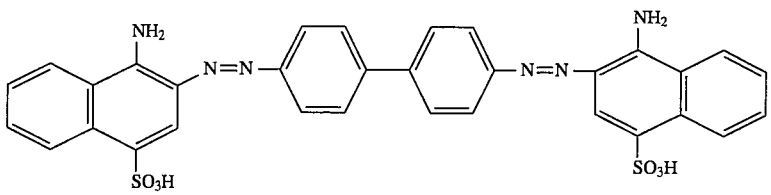
Azo Dye 21
Acid Red 114, C.I. 23635
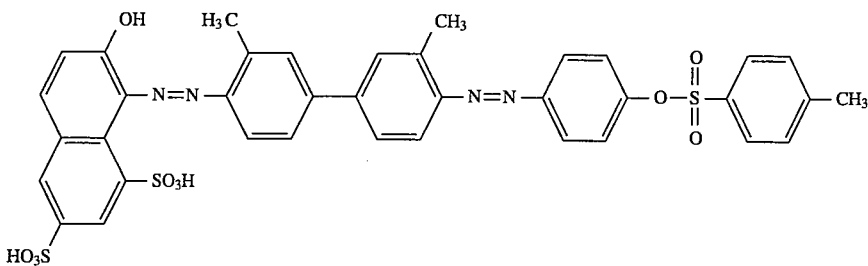

-continued
Azo Dye 22
Direct Blue 15, C.I. 24400
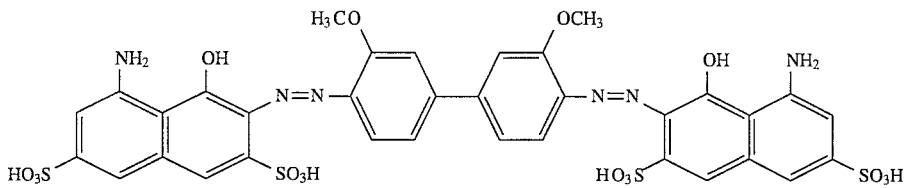
Azo Dye 23
4-(2-hydroxy-1-napthylazo)-1-napthelenesulfonic acid, C.I. 15620
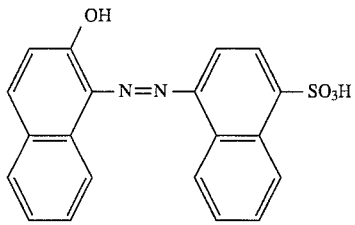
Azo Dye 24
4-(2-hydroxynaphthyl azo)-azobenzene-3,4'-disulfonic acid, Blebrich Scarlet, C.I. 26905
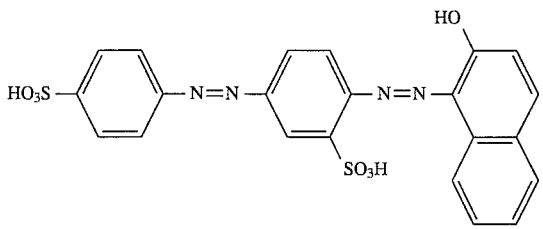
Azo Dye 25
Direct Blue 71, C.I. 34140
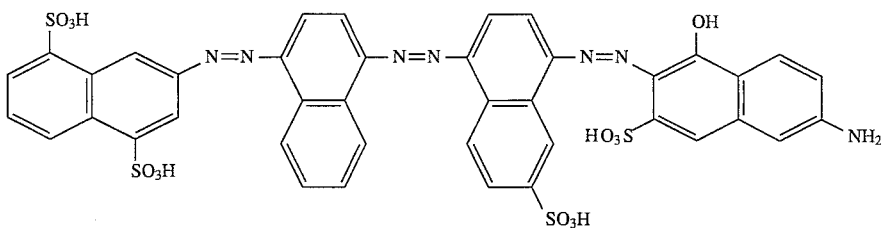
Azo Dye 26
Direct Red 75, C.I. 25380
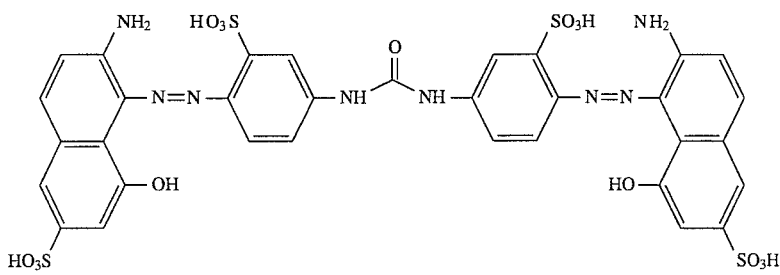

-continued
Azo Dye 27
Chrysophenine, C.I. 24895
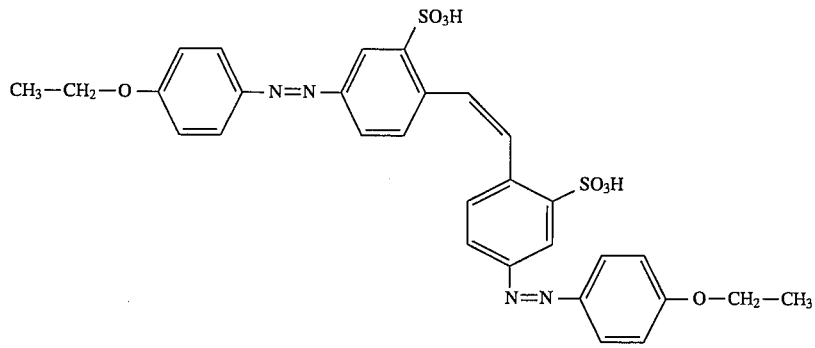
Azo Dye 28
Tartrazine, C.I. 19140
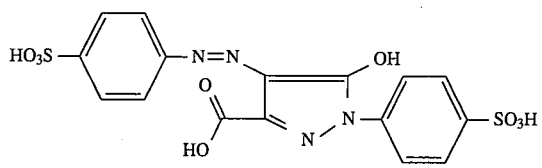
Azo Dye 29
Direct Yellow 27, C.I. 13950
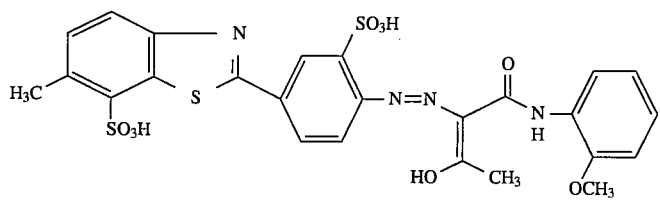
Azo Dye 30
4-aminoazobenzene-4'-sulfonic acid
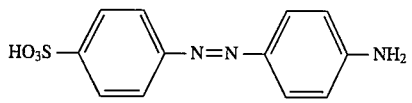
Azo Dye 31
4-(2-hydroxy napththylazo)-benzensulfonic acid
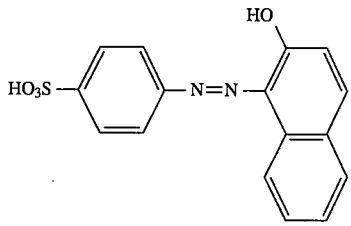
Azo Dye 32
4-(4-hydroxynaphthylazo)-benzenesulfonic acid
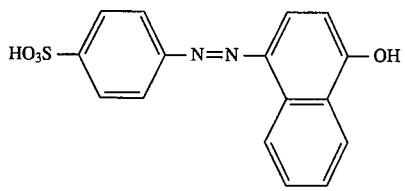

Azo Dye 33
4-(3-Sulfo-4-aminophenylazo)-[U—$^{14}$C]benzenesulfonic acid

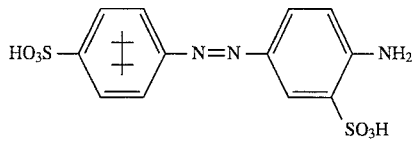

Azo Dye 34
4-(3-Methoxy-4-hydroxyphenylazo-[U—$^{14}$C)]benzenesulfonic acid

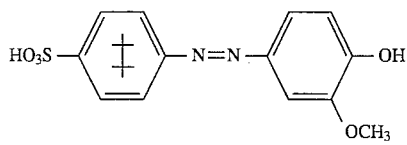

Azo Dye 35
4-(2-Sulfo-3'-methoxy-4'-hydroxyazobenzene-4-azo)-[U—$^{14}$C]benzenesulfonic acid

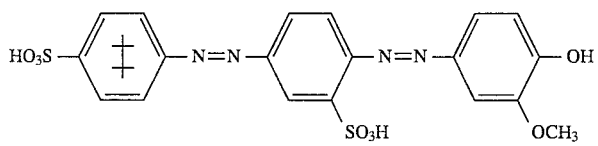

Azo Dye 36
4-(2-Hydroxynaphthylazo)-[U—$^{14}$C]benzenesulfonic acid

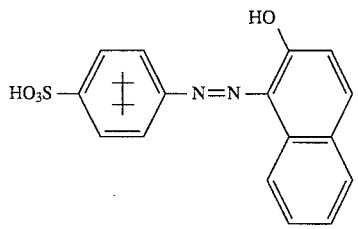

Azo Dye 37
4(4-Hydroxynaphthylazo)-[U—$^{14}$C]benzenesulfonic acid

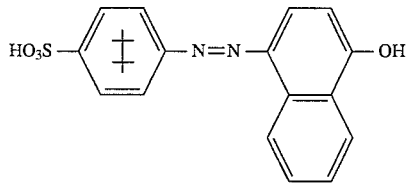

IV. CHEMICAL CHARACTERIZATION OF THE AZO DYES

The purity of all synthesized dyes was analyzed by mass spectra, TLC, and HPLC. Mass spectra (FAB, glycerol as the sample matrix, negative ionization) showed pseudomolecular ions of high intensity, originating from proton losses (M-H)$^-$. There were also very characteristic azo cleavage ions for all examined compounds at m/z 156 and m/z 171 as expected for monosulfonated azo compounds. The mass spectra of azo dye 1 [4-(3-methoxy-4-hydroxyphenylazo)-azobenzene-3,4'-disulfonic acid] and azo dye 2 [3-methoxy-4-hydroxy-azobenzene-4'-sulfonic acid] are shown in FIGS. 1A and 1B respectively. TLC analysis (silica Gel G, n-butanol-acetic acid-water (20:10:50)) confirmed the homogeneity of each of the products. The HPLC analysis of the azo dyes was performed by a slightly modified version of the method of White and Harbin (White et al. "High Performance Liquid Chromatography of Acidic Dyes on a Dynamically Modified Polystyrene-divinylbenzene Packing Material with Multi-Wavelength Detection and Absorbance Ratio Characterization," *Analyst*, 114:877–882 (51)) using as mobile phases (degassed) acetonitrile-water at ratios of 50:50, 60:40, or 70:30, each containing 0.05M dibasic sodium phosphate and 0.01M tetrabutylammonium hydrogen sulfate (TBAH). The HPLC analysis showed purities of the azo dyes to be from about 97% to about 99%.

V. MICROORGANISMS AND CULTURE MAINTENANCE

Twelve wild-type actinomycetes were selected from 20 strains isolated from higher termites in Kenya. Pasti and Belli, *FEMS Microbiol. Lett.*, 1985, 26:107–112. All strains have been identified as Streptomyces, based on the key of Williams, et al. *J. Gen. Microbiol.*, 1983, 129:1815–1830. The strains listed in Table 3 are those strains identified as Streptomyces by Pasti and Belli. *Streptomyces viridosporus* T7A (ATCC 39115) was isolated from soil by D. L. Sinden (M.S. thesis, University of Idaho, Moscow, 1979). *Streptomyces badius* 252 (ATCC 39117) was isolated from soil by Phelan et al. (*Can. J. Microbial*, 1979, 27:636–368) and Streptomyces SR-10 is a protoplast fusion recombinant derived from a cross between *S.viridosporus* T7A and *S. setonii* 75Vi2. Pette and Crawford, *Appl. Environ. Microbiol.*, 1984, 47:439–440. Stock cultures of the Kenyan isolates were maintained at 4° C., after growth and sporulation at 37° C. on the following medium as specified in grams-per-liter of deionized water: $NH_4NO_3$, 1; $KH_2PO_4$, 0.4; yeast nitrogen base (Difco), 0.67; yeast extract (Difco), 0.2; lactose, 15; bacto-agar (Difco), 18. *S. viridosporus* T7A, *S. badius* 252 and S. SR-10 were maintained at 4° C., after growth and sporulation at 37° C. on yeast extract-malt extract dextrose agar, as in Pridham and Gottlieb, *J. Bacteriol.*, 1948, 56:107–114. Stock cultures were subcultured every 2 to 10 weeks, and distilled water suspensions of sporulated growth were used as initial inocula in all experiments. *S. chromofuscus* A11 (ATCC 55184) was selected from 20 strains isolated from higher termites in Kenya.

*Phanerochaete chrysosporium* Burds BKM-C-1767 (ATCC 24725) was used for the mineralization of radiolabeled compounds. *Phanerochaete chrysosporium* Burds BKM-1667 (ATCC 24725) was grown in 125-ml flasks. Filter-sterilized concentrated stock solutions were used to prepare the final medium. The mineral salts stock solution contained 10 g L-asparagine, 5 g $NH_4NO_3$, 20 g $KH_2PO_2$, 5 g $MgSO_4 \times 7\ H_2O$, 1 g $CaCl_2 \times 2\ H_2O$, 0.05 g thiamine, 100 ml trace elements (6), and water to 1000 ml. Other stock solutions consisted of 20% glucose; 1M sodium 2,2'-dimethylsuccinate (pH 4.5); and 0.75 g phenylalanine and 0.275 g adenine in 1 liter of distilled water.

*Phanerochaete chrysosporium* BKM-F-1767 (ATCC 24725) was obtained from The Forest Products Laboratory, Madison, Wis. The fungus was maintained and spore inocula were prepared as previously described by Huynh and Crawford, *FFMS Microbiol. Lett.*, 1985, 28:119–123.

All these publications describing isolation of the Streptomyces and Phanerochaete, and all publications describing culture maintenance, are incorporated by reference.

VI. CULTURE CONDITIONS FOR BIODEGRADATION

A. Actinomycete Cultures

Each Streptomyces species was grown in a cotton-plugged 250 ml flask containing 25 ml of the following medium: 0.2M Tris buffer (pH 7.6), 100 ml; vitamin-free Casamino acids (Difco), 1.0 g; thiamine, 100 μg; biotin, 100 μg; D-glucose, 2 g; deionized water, 900 ml. Thiamine, biotin and D-glucose were filter-sterilized and added to the autoclaved medium, as in McCarthy and Broda, *J. Gen. Microbiol.*, 1984, 130:2905–2913.

The dyes were filter-sterilized and added at 0.005% (w/v) to the autoclaved basal medium. Alternatively, azo dye stock solutions were sterilized by filtration (pore size 0.2 μm) and added to autoclaved basal medium at concentrations of 50 or 100 ppm. Three replicates of every culture were incubated, and each strain was grown in media supplemented individually with every substrate. Replicate sterile controls also were run in each experiment. Cultures were incubated at 37° C. for 14 days with shaking (200–250 rpm). Three replicates for each strain growth were incubated in only the basal medium as well.

B. *Phanerochaete Chrysosporium*

*Phanerochaete chrysosporium* was grown in a cotton-plugged 500 ml flask containing 250 ml defined medium (Jeffries, et al., *Appl. Environ. Microbiol.*, 1981, 42:290–296), with the addition of 75 mg adenine (6-aminopurine) and 27 mg L-phenylalanine-per-liter. This addition accelerated the growth of the fungus without inhibiting ligninase activity. Azo dye stock solutions were sterilized by filtration (pore size 0.2 μm). Four substrates were initially tested: sulfanilic acid, acid yellow 9 and azo dyes 1 and 2. Each substrate was separately added at a concentration of about 0.02% (w/v). Cultures were incubated at 37° C. for 7 to 15 days with shaking (250 rpm). Solid agar media were also employed. The medium was 3.0% (w/v) malt extract (Difco Laboratories) agar dispensed in petri plates. Otherwise, azo dye substrates were typically added to autoclaved basal medium at concentrations of from about 150 ppm to about 300 ppm.

VII. PROTEIN DETERMINATIONS

Intracellular protein concentration was used as an index of culture growth. Intracellular protein concentration was determined by boiling harvested culture pellets for 20 minutes in 1M NaOH. Protein concentration was then determined by Sigma calorimetric procedure No. TPRO-562. Extracellular protein was determined using culture filtrates and Bio-Rad calorimetric procedure No. 500-0006.

VIII. SPECTROPHOTOMETRIC ASSAY

A one ml sample of culture medium was centrifuged and then diluted 2.5–5.0 fold (actinomycete culture) or 5- to 10-fold (fungal culture) with distilled water. Alternatively, 1.0 ml of fungal supernatant was centrifuged and diluted 5-fold with 10 mM sodium 2,2-dimethylsuccinate buffer (DMS) of pH 4.5. Azo dye substrate present was then measured spectrophotometrically with a Hewlett-Packard 8452 diode array spectrophotometer operated by a PC Vectra computer equipped with HP's MS™-DOS/UV-VIS software. To be certain that changes in substrate spectra were not due to pH variations, the effects of pH on the visible absorption of each compound were also assayed within physiological pH range in the culture media. While the spectra of sulfanilic acid (Max abs at 250 nm), vanillic acid (Max abs at 252 nm and 286 nm) and acid yellow 9 (Max abs at 336 nm) were unaffected by pH over the tested pH range, the spectra of several novel azo dyes were changed as evidenced by shifts of their $Abs_{max}$. Thus, the spectrophotometric assays for the dyes were typically carried out at their isobestic points. For instance, the spectrophotometric assays were carried out at 450 nm for azo dye 1 and 400 nm for azo dye 2. Spectrophotometric measurements were carried out at the absorbance maxima for azo dyes 16, 17, 18, 19, 31, and 32 (See Table 1 below). Since the spectra of the remaining dyes were affected by pH within the physiological pH range, spectrophotometric assays were carried out at the isobestic points (See Table 1). The compounds were quantified by first developing standard curves of absorbance versus concentrations (0–50 μg) and then comparing measured absorbance values to the standard curves.

TABLE 1 pH-dependent wavelength shifts of azo dyes tested in this biodegradation study. Corresponding e values are included.

| Azo Dye No. | 0.01M HCl Max Wav. | Loge | 0.01M Tris Max Wav. | Loge | 0.01M NaOH Max Wav. | Loge | Isobestic point Max Wav. | Loge |
|---|---|---|---|---|---|---|---|---|
| 1  | 394 | 4.414 | 400 | 4.360 | 520 | 4.532 | 450 | 4.263 |
| 2  | 370 | 4.304 | 370 | 4.290 | 466 | 4.498 | 400 | 4.124 |
| 3  | 362 | 4.329 | 360 | 4.322 | 470 | 4.493 | 394 | 4.032 |
| 4  | 380 | 4.128 | 380 | 4.128 | 494 | 4.448 | 418 | 3.967 |
| 5  | 360 | 4.310 | 360 | 4.296 | 458 | 4.440 | 388 | 4.113 |
| 6  | 354 | 4.342 | 354 | 4.256 | 438 | 4.209 | 384 | 4.035 |
| 7  | 338 | 4.161 | 338 | 4.159 | 492 | 3.870 | 430 | 3.669 |
| 8  | 328 | 4.296 | 328 | 4.290 | 492 | 4.014 | 424 | 3.756 |
| 9  | 328 | 4.206 | 328 | 4.216 | 492 | 3.931 | 420 | 3.660 |
| 10 | 348 | 4.362 | 348 | 4.293 | 456 | 4.148 | 398 | 3.944 |
| 11 | 342 | 4.216 | 344 | 4.231 | 354 | 4.021 | 406 | 3.568 |
| 12 | 348 | 4.312 | 420 | 4.312 | 420 | 4.327 | 376 | 4.085 |
| 13 | 352 | 4.374 | 436 | 4.324 | 436 | 4.150 | 378 | 4.150 |
| 14 | 504 | 4.569 | 466 | 4.339 | 466 | 4.337 | 470 | 4.329 |
| 15 | 508 | 4.276 | 474 | 4.512 | 474 | 4.512 | 514 | 4.254 |
| 16 | 352 | 4.329 | 352 | 4.294 | 352 | 4.274 | 414 | 3.563 |
| 17 | 368 | 4.052 | 368 | 4.245 | 368 | 3.964 | 424 | 3.646 |
| 18 | 386 | 4.360 | 386 | 4.392 | 386 | 4.395 | 446 | 4.047 |
| 19 | 484 | 4.273 | 484 | 4.272 | 428 | 3.937 | 436 | 3.929 |
| 30 | 486 | 4.075 | 388 | 4.324 | 388 | 4.321 | 462 | 3.963 |
| 31 | 484 | 4.367 | 484 | 4.367 | 484 | 4.146 | 525 | 3.986 |
| 32 | 475 | 4.491 | 475 | 4.491 | 514 | 4.477 | 492 | 4.415 |

IX. HIGH PERFORMANCE LIQUID CHROMATOGRAPHY ANALYSIS

Degradation of the dyes and aromatic compounds was confirmed by high performance liquid chromatography. A Hewlett-Packard HP 1090 Liquid Chromatograph equipped with a HP 40 diode array UV-VIS detector and automatic injector was used. The chromatograph was controlled by an HP 9000 series 300 computer which used HP 7995 A ChemStation software. A reverse phase column from Phenomenex (Rancho Palos Verdes Calif., type Spherex 5 C 18 size 250×2.0 mm, serial number PP/6474A) was used. Each 15 minute analysis used a solvent gradient of acetonitrile (solvent A) and 10 mM DMS buffer pH 4.5 (solvent B), with the following conditions: 0 to 5 minutes 100% A; 5 to 12 minutes 25% A 75% B; 12 to 15 minutes 100% B; post time 2 minutes injection volume 10 µl. Absorption was measured at 250, 325, 350, 400 and 450 nm, and spectra were collected automatically by the peak controller.

X. PREPARATION OF ENZYMES AND ENZYME ASSAYS

A. Actinomycetes

Streptomyces species peroxidases were prepared and assayed using 2,4-dichlorphenol as a substrate as described in Ramochaondra et al., *Appl. Environ. Microbiol.*, 1988, 54:3057–3063. In more detail but without limitation, *Streptomyces chromofuscus* A11, which is generally representative of the streptomycetes, was inoculated into 1500 ml of media described by Crawford et al, "The Effect of Various Nutrients on Extracellular Peroxidases and APPL Production by *Streptomyces chromofuscus* A2 and *Streptomyces viridosporus* T7A," *Appl. Microbiol. Biotechnol.*, 34:661–667. Incubation took place at 37° C. with shaking at 250 rpm. The culture supernatant was collected after 48 h incubation, and vacuum-filtered through Whatman no. 1 filter paper. The filtrate was concentrated approximately 40- to 50-fold by ultrafiltration through an Amicon ultrafiltration stirred cell (series no. 8000, Amicon Corp.) with a disc PM-10 filter (diameter, 76 mm). Protein in the concentrated filtrate was then precipitated from solution with 80% ammonium sulfate. The precipitate was collected by centrifugation (15 min, 10,000 rpm). The pellet was resuspended in 10 ml of 20 mM HEPES buffer (pH 8) and dialyzed overnight against the same buffer at 4° C. These preparations were then stored in 1-ml aliquots at −20° C. until used. Before using, the preparation was filtered through a NAP-25 Sephadex G-25 disposable column (Pharmacia) in order to separate a yellowish protein fraction from a pink low-molecular-weight fraction. The yellowish fraction was used as the source of enzyme.

The peroxidase assay was carried out using a composition having a final volume of 1.0 ml. The reaction mixture contained 250 µl of 100 mM HEPES buffer (pH 8), 500 µl of 10 mM 2,4-dichlorophenol, 100 µl of 1 mM aminoantipyrine, 50 µl enzyme preparation and 100 µl 50 mM $H_2O_2$. The reaction was initiated by the addition of hydrogen peroxide at 37° C. One unit of peroxidase activity was expressed as the amount of enzyme required for an increase of one absorbance-unit-per-minute at 510 nm. Assays of manganese peroxidase and of ligninase from *P. chrysosporium* were carried out as previously described by Paszczynski et al in "Manganese peroxidase of Phanerochaete chrysosporium: Purification," *Methods Enzymol.* 161:264–270, incorporated herein by reference. One unit of Mn(II)-peroxidase was defined as the amount of enzyme required for oxidation of 1 µmol of vanillylacetone-per-minute; one unit of ligninase was defined as the amount of enzyme required for production of 1 µmol of veratryl aldehyde-per-minute. When veratryl alcohol was added, the final concentration in the reaction mixture was 1 mM.

B. *Phanerochaete Chrysosporium*

*P. chrysosporium* BKM-F-1767 was grown in a 20-liter carboy containing one liter of nitrogen-limited defined medium (BII-medium), as described by Paszczynski, et al., *Arch Biochem. Biophys.*, 1986, 44:750–765. Preparation and assay of ligninase and manganese peroxidase from these *P. chrysosporium* cultures were carried out as previously reported by Paszczynski, et al., *Methods Enzymol.*, 1988, 161:264–270.

XI. OXIDATION OF DYES BY ENZYME PREPARATIONS

A. Oxidation Conditions

The oxidation of azo dyes by *S. chromofuscus* A11 crude enzyme preparation was carried in an assay mixture containing 800 µl of 100 mM HEPES (pH 8), 5 µl of azo dye solution (5 mg/ml), and 100 µl crude enzyme preparation (activity: 7.5 absorbance unit/minute/ml; protein content: 2.88 mg/ml). The reaction was started with the addition of 100 µl of 50 mM $H_2O_2$ and was followed for 1 min at 37° C. Controls were run with no addition of $H_2O_2$ or with the addition of the hemeperoxidase inhibitor KCN (final concentration 25 µM).

Oxidation of azo dyes by 5 µl of horseradish peroxidase solution (activity: 833 IU/minute/ml; protein content; 0.24 mg/ml) were carried out similarly.

The oxidation of azo dyes by 5 µl of *P. chrysosporium* crude enzyme preparation (protein content: 2.3 mg/ml) was carried out for each dye under two conditions, one specific for Mn(II)-peroxidase (activity: 735 IU/minute/ml) and the second specific for ligninase (activity: 694 IU/minute/ml) Paszczynski et al.'s "Manganese peroxidase of *Phanerochaete chrysosporium*: Purification," *Methods Enzymol.* 161:264–270.

B. *P. Chrysosporium*

Figure 4A:
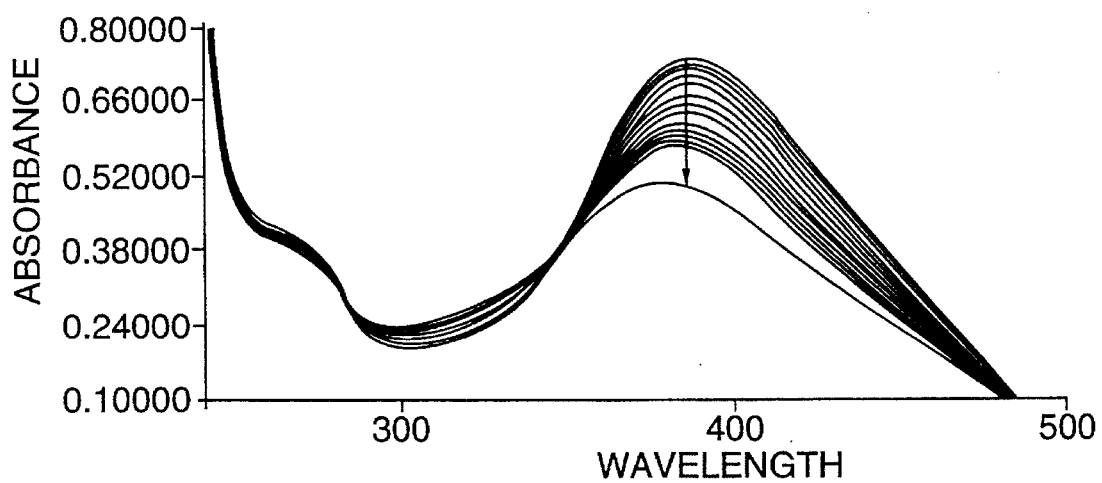
FIG. 4A shows the absorbance spectra over time of acid yellow 9, illustrating its oxidation by *P. chrysosporium* ligninase.
Figure 4B:
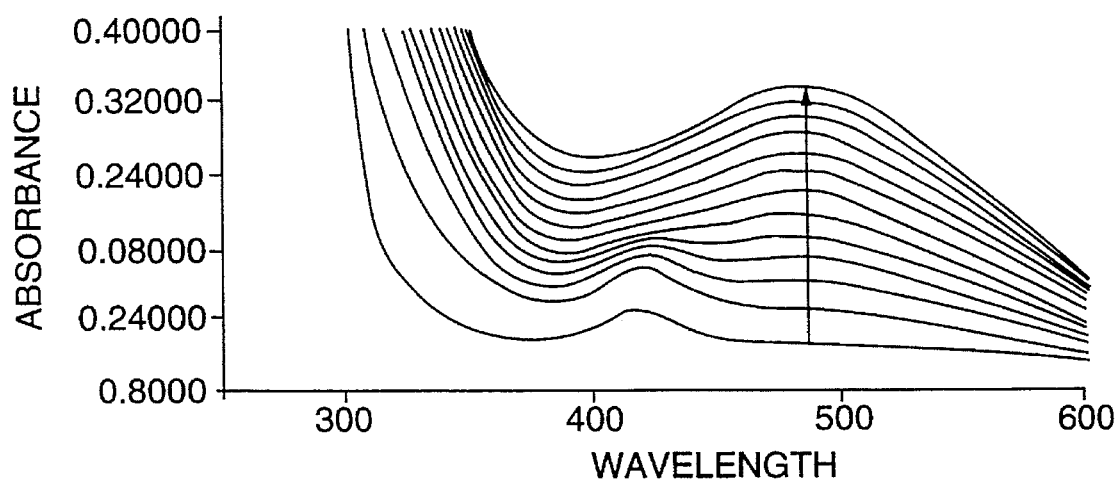
FIG. 4B shows absorbance spectra over time of sulfanilic acid, illustrating its oxidation by *P. chrysosporium* ligninase.

The decolorization of acid yellow 9 azo dye and the oxidation of sulfanilic acid by extracellular preparations of *Phanerochaete chrysosporium* enzymes is shown in FIGS. 4A and 4B, respectively. FIG. 4A shows oxidation of acid yellow 9 by ligninase. The reaction conditions were 0.2 mM hydrogen peroxide, 50 mM sodium tartrate buffer, pH3, 10 µg of dye, and 0.6 units of enzyme (20 µl) in total volume of 1 ml. Cycle time was 30 seconds with the last measure after 15 minutes. During a period of 15 minutes the ligninase exhibited a stable activity which decolorized about 3 micrograms out of 10 micrograms of acid yellow 9 in the reaction mixture. FIG. 4B shows oxidation of sulfanilic acid which was transformed slowly by ligninase, with an increase in absorbance at about 480 nm. The reaction conditions were the same as for acid yellow 9. No decolorization of the synthesized dyes by ligninase was detected.

Figure 4C:
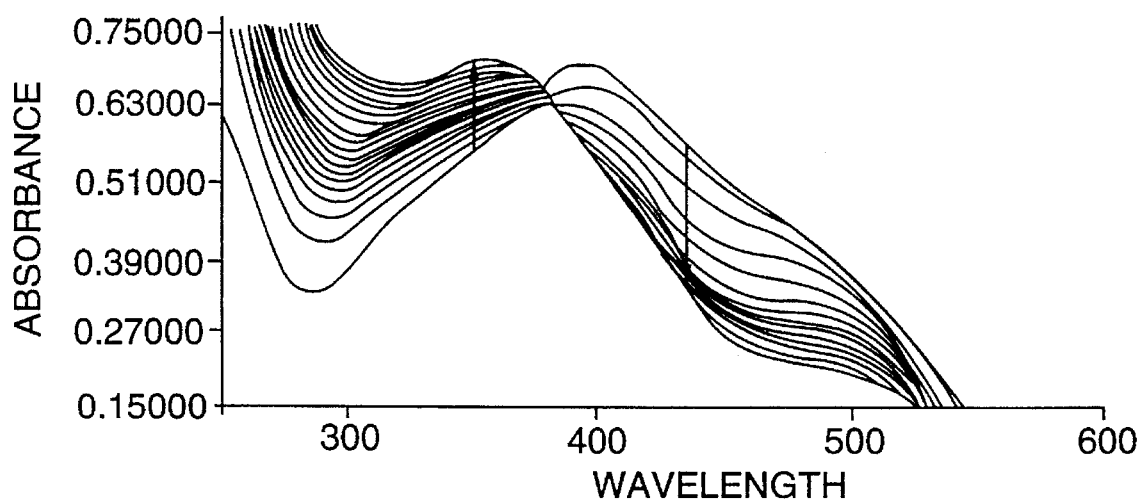
FIG. 4C shows absorbance spectra over time of azo dye 1, illustrating its oxidation by *P. chrysosporium* manganese peroxidase.
Figure 4D:
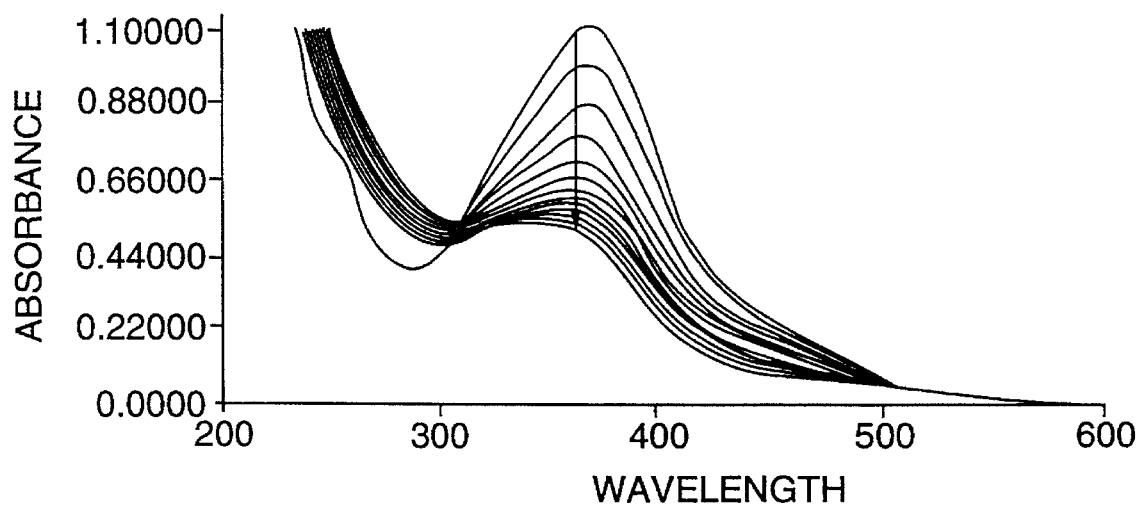
FIG. 4D shows absorbance spectra over time of azo dye 2, illustrating its oxidation by *P. chrysosporium* manganese peroxidase.
Figure 5:
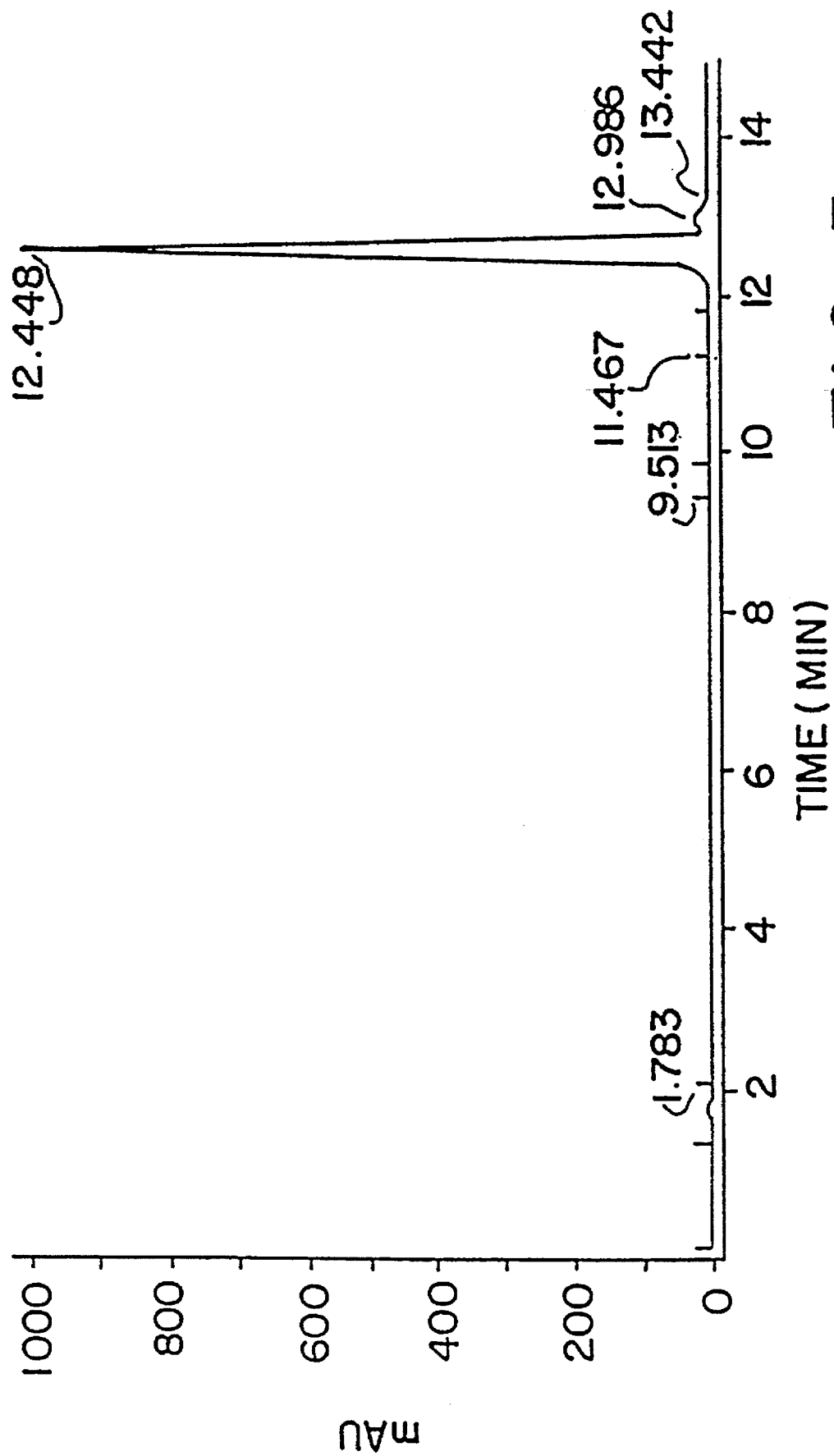
FIG. 5 shows the results of a high performance liquid chromatography (HPLC) of azo dye 1 before (A) and after (B) incubation with *P. chrysosporium* manganese peroxidase, confirming degradation of the dye and aromatic compounds.

FIGS. 4C and 4D show decolorization of azo dyes 1 and 2 by the manganese peroxidase of *P. chrysosporium*. Reaction conditions were 0.2 mM hydrogen peroxide, 50 mM sodium tartrate buffer, pH5, 10 µg dye, 1 unit of enzyme, 1 mM MnSO$_4$ in a total volume of 1 ml. Cycle time was 10 seconds, with the last measure after three minutes of incubation. Oxidation of azo dye 1 by manganese peroxidase resulted in new peak formation at 355 nm. After one hour incubation of azo dye 1 with manganese peroxidase the dye was almost completely degraded comparable to a control chromatogram (FIG. 5). No decolorization of acid yellow 9 or oxidation of sulfanilic acid by manganese peroxidase was detected.

C. Streptomyces

Figure 10A:
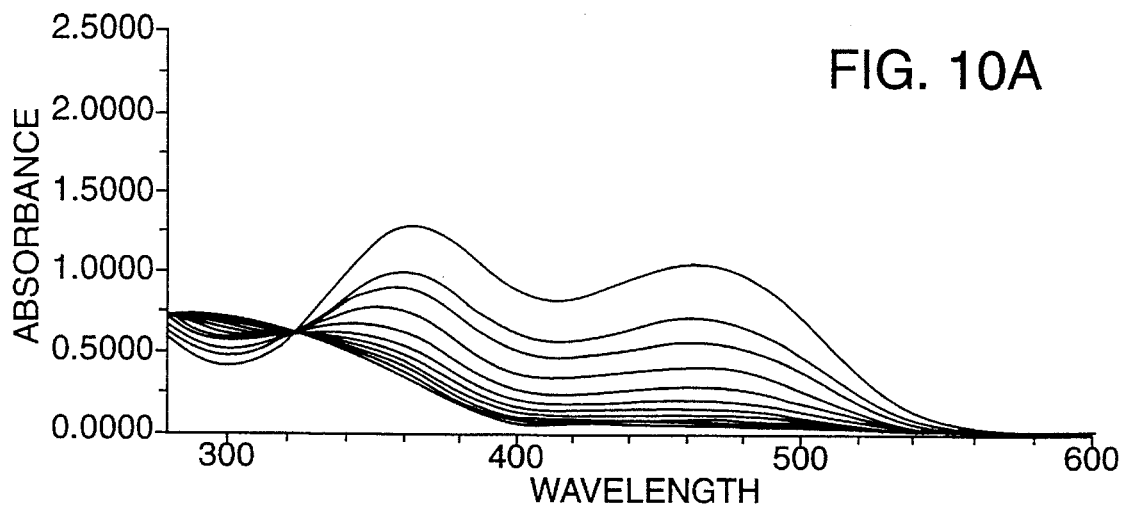
FIG. 10A is an absorbance spectra versus wavelength that shows the oxidation of azo dye 3 by commercial horseradish peroxidase II.
Figure 10B:
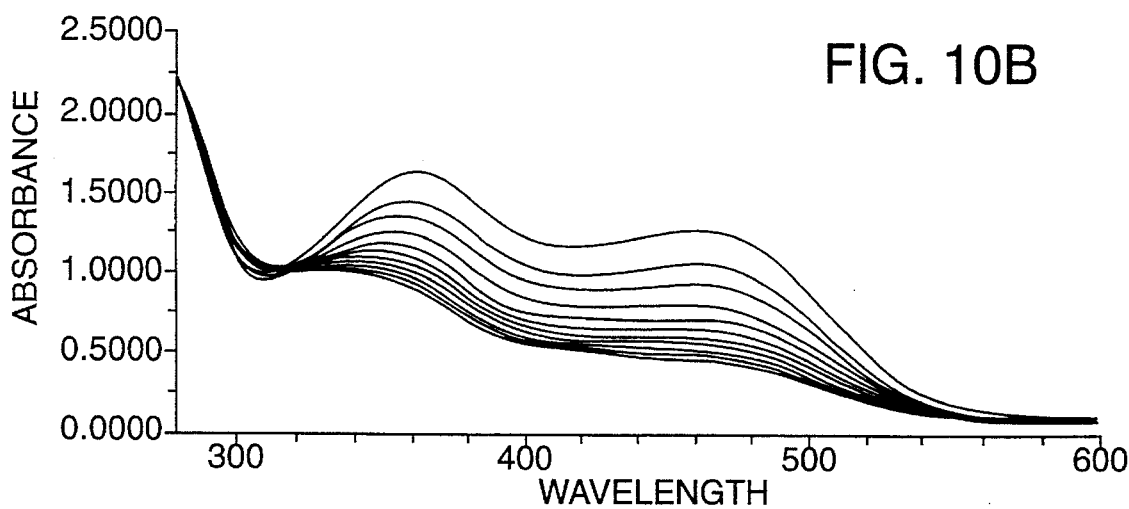
FIG. 10B is an absorbance spectra versus wavelength that shows the oxidation of azo dye 3 by *S. chromofuscus* A11 enzyme preparation.
Figure 10C:
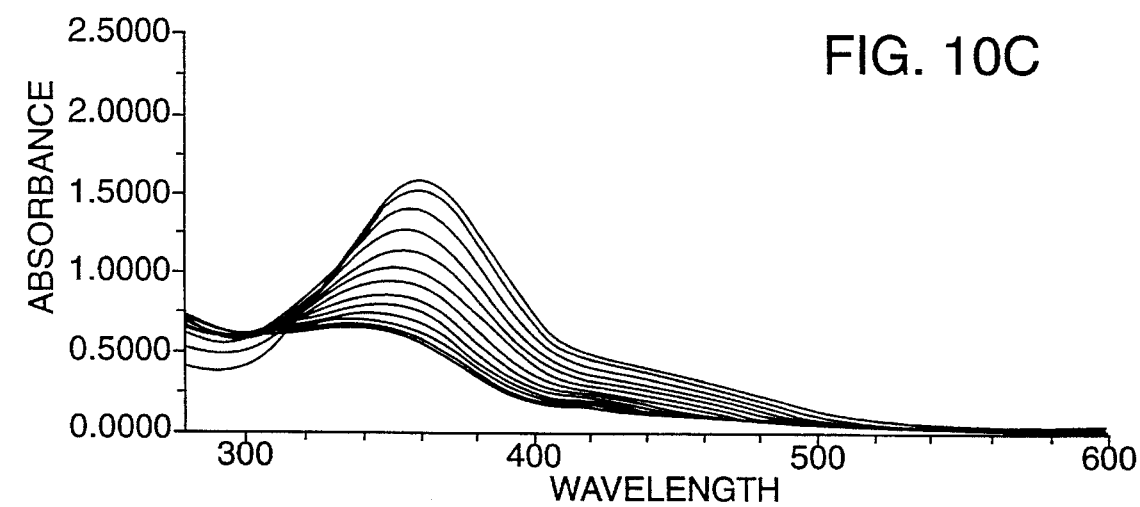
FIG. 10C is an absorbance spectra versus wavelength that shows the oxidation of azo dye 3 by *P. chrysosporium* Mn(II) peroxidase.

The azo dyes were not decolorized by *S. chromofuscus* A11 enzyme preparations without the addition of H$_2$O$_2$. Furthermore, dye decolorization was drastically inhibited by the addition of KCN. Table 2 shows the result of the spectrophotometric assays using the enzyme preparations of *S. chromofuscus* A11 and *P. chrysosporium*, and by horseradish peroxidase type II. Azo dyes 1–5 and 32 were the only dyes decolorized by the streptomycetes and by the commercial preparation of horseradish peroxidase. Streptomycetes decolorizes only those dyes that were also oxidized mainly by the Mn(II)-peroxidase component of the fungal ligninolytic system. FIG. 10 shows the change in spectra of azo dye 3 during oxidation by horseradish peroxidase (FIG. 10a), by *S. chromofuscus* A11 enzyme preparation (FIG. 10b), and by *P. chrysosporium* Mn(II)-peroxidase (FIG. 10c). Dye 12 was an extraordinarily specific substrate for ligninase. When ligninase was involved in oxidizing the azo dye, the addition of veratryl alcohol enhanced the oxidation rate of virtually all dyes about 100%. See further discussion regarding veratryl alcohol below.

TABLE 2

Oxidation rate of azo dyes (µmoles per minute per ml) by horseradish peroxidase preparation, by *S. chromofuscus* A11, and by *Phanerochaete chrysosporium* crude enzyme preparations.

| Azo dye No. | Horseradish peroxidase | *S. chromofuscus* peroxidase | Mn-peroxidase | *P. chrysosporium* Ligninase |
|---|---|---|---|---|
| 1  | 8.24  | 1.78  | 3.06  | 0.44  |
| 2  | 18.19 | 3.68  | 8.19  | 0.72  |
| 3  | 30.68 | 17.20 | 16.37 | 0.42  |
| 4  | 27.04 | 15.19 | 14.33 | 0.22  |
| 5  | 11.94 | 2.00  | 3.54  | 0.00  |
| 6  | 0.47  | 0.42  | 0.02  | 0.45  |
| 7  | 0.34  | 0.19  | 0.11  | 1.35  |
| 8  | 0.07  | 0.14  | 0.32  | 0.49  |
| 9  | 0.20  | 0.35  | 0.07  | 1.27  |
| 10 | 0.35  | 0.78  | 2.86  | 0.51  |
| 11 | 0.15  | 0.33  | 1.06  | 1.28  |
| 12 | 0.17  | 0.15  | 0.00  | 11.61 |
| 13 | 0.10  | 0.13  | 0.26  | 0.88  |
| 14 | 0.07  | 0.10  | 0.15  | 0.32  |
| 15 | 0.12  | 0.17  | 0.23  | 0.75  |
| 16 | 0.06  | 0.06  | 0.00  | 0.25  |
| 17 | 0.32  | 0.50  | 0.72  | 1.03  |
| 18 | 0.12  | 0.15  | 0.09  | 1.38  |
| 19 | 0.08  | 0.35  | 0.10  | 2.06  |
| 30 | 0.40  | 0.00  | 0.59  | 1.58  |
| 31 | 0.52  | 0.09  | 0.47  | 1.18  |
| 32 | 3.91  | 2.62  | 4.62  | 0.23  |

Apparently a hemeperoxidase is responsible for azo dye decolorization because *S. chromofuscus* A11 enzyme preparations failed to decolorize dye in the absence of H$_2$O$_2$, and the enzyme preparations were drastically inhibited by the addition of KCN, a hemoprotein inhibitor. The lignin-degrading system of *P. chrysosporium* contains a number of peroxidases that can catalyze the depolymerization of lignin, as well as the initial oxidation of a wide range of other compounds. Streptomycetes also oxidatively depolymerize lignin, with extracellular peroxidases apparently participating in the lignin solubilization process.

When an azo dye was a more suitable substrate for fungal ligninase than for Mn(II)-peroxidase, the streptomycetes were unable to oxidize the dye (Table 2). While Acid Yellow 9 (azo dye 18) remained untouched by the streptomycetes cultures and was oxidized by *P. chrysosporium* lignin peroxidase, the synthesized azo dyes 1 and 3 were decolorized by five selected streptomycetes cultures and oxidized by *P. chrysosporium* Mn(II)-peroxidase. Apparently, extracellular peroxidases produced by lignocellulolytic Streptomyces spp. are similar in substrate specificity to horseradish peroxidase type II and to the Mn(II)-peroxidases of *P. chrysosporium*.

Dye 12 was oxidized only by ligninase. A possible explanation, without limitation, is that fluorine atoms withdraw electrons from the aromatic ring, making it more difficult for peroxidases with lower oxidation potential than that of ligninase [i.e., Mn(II)-peroxidase] to form cation radicals. However, azo dye 3, having methyl groups ortho to the 4-hydroxy group, which are electron-releasing substituents, was a preferred substrate for peroxidases with low oxidation potentials. Hence, azo dyes 3 and 12 can be used to assay specific bacterial or fungal peroxidases.

Such an assay would comprise oxidizing each of the azo dyes with peroxidase and determining the extent to which each azo dye is oxidized. If azo dye 12 is extensively oxidized, then a ligninase is involved. If azo dye 3 is oxidized, but azo dye 12 is not, then a peroxidase is involved.

XII. Biotransformation of Microorganisms

A. Streptomyces

Table 3 shows the substrate utilization pattern of the Streptomyces species after a growth period of 14 days. Only six strains (A4, A10, A11, A12, A13, and A14) significantly degraded vanillic acid, while none degraded sulfanilic acid or acid yellow 9 to a detectable extent. Significant degradation was considered degradation greater than about 10%. This result confirms that the compounds characterized by aromatic sulfo group and azo linkages are quite recalcitrant. However, 5 strains (A10, A11, A12, A13, and A14) significantly degraded both the two new azo dyes. Moreover, azo dye 2 was degraded by these strains to a larger extent than azo dye 1.

TABLE 3

Percent substrate removed by cultures of Streptomyces and Phanerochaete during a growth period of 14 and 7 days respectively

| Strain | Sulfanilic acid | Vanillic acid | Acid Yellow #9 | Azo dye #1 | Axo dye #2 |
|---|---|---|---|---|---|
| S. chromofuscus A2 | — | — | — | — | — |
| S. diastaticus A3 | — | — | — | — | — |
| S. rochei A4 | — | 100 | — | — | — |
| S. chromofuscus A6 | — | — | — | — | — |
| S. cyaneus A7 | — | — | — | — | — |
| S. chromofuscus A8 | — | — | — | — | — |
| S. rochei A10 | — | 91 | — | 51 | 74 |
| S. chromofuscus A11 | — | 100 | — | 56 | 89 |
| S. diastaticus A12 | — | 58 | — | 27 | 30 |
| S. diastaticus A13 | — | 34 | — | 15 | 21 |
| S. rochei A14 | — | 72 | — | 43 | 72 |
| S. chromofuscus A20 | — | 5 | — | 1 | 11 |
| S. viridosporus T7A | — | 3 | — | 1 | 9 |
| S. SR-10 | — | — | — | — | — |
| S. badius 252 | — | 7 | — | 9 | 18 |
| P. chrysosporium | 68 | n.d. | 79 | 93 | 94 |

Figure 2:
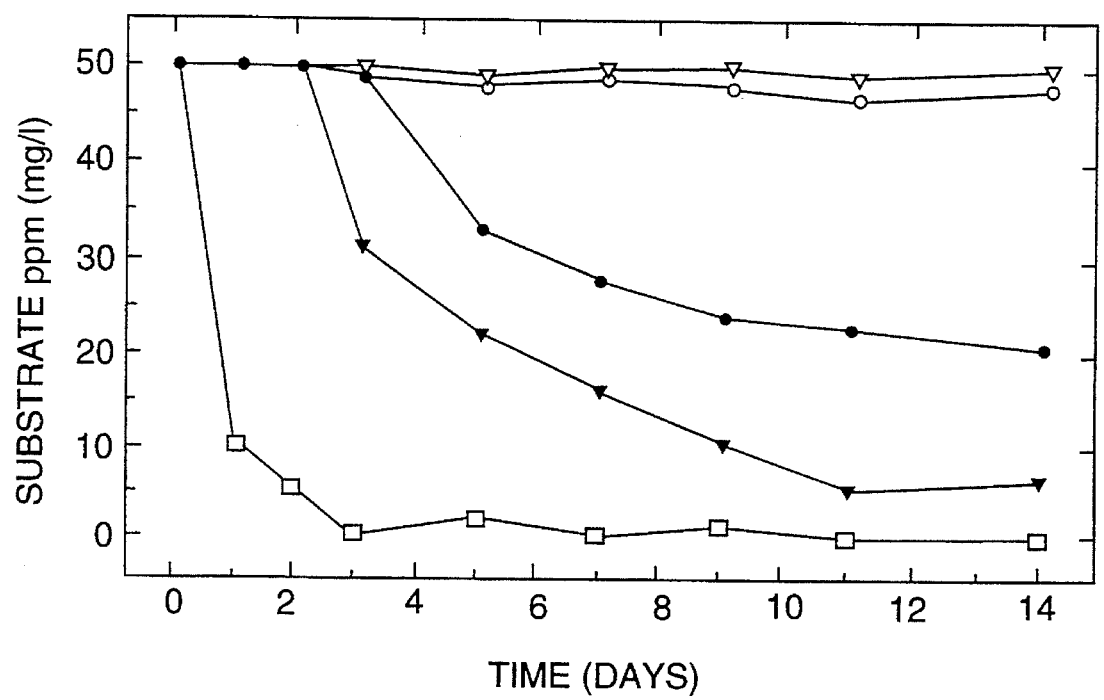
FIG. 2 is a graph showing the degradation by *Streptomyces chromofuscus* A11 of vanillic acid, sulfanilic acid, Acid Yellow 9, and two of the azo dyes synthesized in accordance with the present invention.

FIG. 2 shows the pattern of degradation of each compound by strain S.chromofuscus A11 versus time, as a typical example. The graph shows the degradation of vanillic acid (□), sulfanilic acid (▽), acid yellow 9 (○), and azo dyes 1 (●) and 2 (▼). The medium contained 0.2M Tris buffer (pH 7.6), 100 ml; vitamin-free casamino acids, 1.0 g; thiamine, 100 μg; biotin, 100 μg; D-glucose, 2 g; and deionized water, 900 ml. Starting substrate concentrations were 50 ppm. P. chrysosporium degraded sulfanilic acid and acid yellow 9, but only to a limited extent. The vanillic acid, in contrast, was rapidly and thoroughly degraded, as were azo dyes 1 and 2. The ring substitution patterns for vanillic acid, sulfanilic acid, guaiacol, and syringyl are shown below:

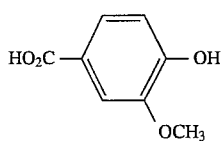

-continued
Vanillic acid
4-hydroxy-3-methoxy-benzoic acid

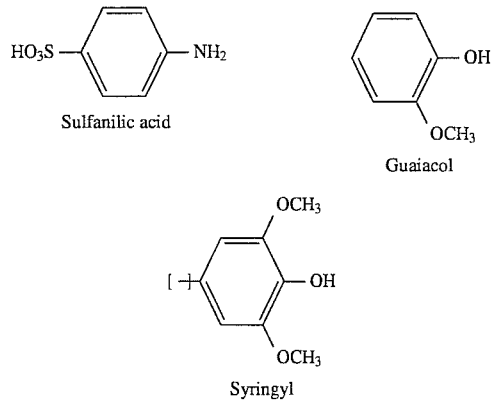

It appears that the linkage of a guaiacol moiety into azo dye yellow 9 allowed Streptomyces species capable of utilizing vanillic acid to decolorize an azo dye that the Streptomyces could not otherwise transform. The only vanillic acid degrader that could not attack either azo dyes 1 or 2 was S. rochei A4, possibly because this strain catabolizes vanillic acid by attacking its carboxylic acid group, a substituent absent in the guaiacol moiety. Hence, utilization of the two dyes appears to start at the guaiacol substituent, but the pathway used by these Streptomyces remains to be elucidated.

S. chromofuscus A11 was chosen as a representative microorganism for further study of the degradation pattern. Table 4 below shows the degradation of 19 azo dyes and 3 controls (Acid Yellow 9 [dye 17], the negative control; and azo dyes 1 and 2, the positive controls) by S. chromofuscus A11, as measured by decolorization of the growth medium. Five dyes (3, 4, 5, 10 and 32) were significantly decolorized at both 50 and 100 ppm. Less decolorization of azo dyes 1, 3 and 5 occurred at the higher than at the lower concentration (Table 4). This may mean that these dyes are more toxic than the remaining azo dyes. For cultures of Streptomyces A11, the highest decolorization seemed to occur between day 2 and day 5 for all dyes at a dye concentration of 50 ppm. The decolorization values from spectrophotometric data were checked by HPLC analyses, confirming the disappearance of the compounds.

Significant degradation of the azobenzene derivative dyes (dyes 1–18 and 30) by actinomycetes occurred when the hydroxy group was in the para position to the azo linkage and at least one or two electron-releasing substituents were ortho to the hydroxy group (Table 4; azo dyes 1–4, 9). Degradation of the naphthol-derivative azo dyes (dyes 19, 31, and 32) occurred when the hydroxy group was in the 4-position to the azo linkage. The second condensed aromatic ring in naphthalene apparently acts as an electron-donating fragment, similar to the electron-releasing substituents in the benzene ring of dyes 3–5 and 10.

TABLE 4

Azo dye decolorization by microorganisms *Streptomyces chromofuscus* A11 and by *Phanerochaete chrysosporium* over a growth period of 14 days.

| | % Decolorization | | | |
|---|---|---|---|---|
| | *S. chromofuscus* A11 Initial concn (ppm) | | *P. chrysosporium* Initial concn (ppm) | |
| Azo dye | 50 | 100 | 150 | 300 |
| 1[a] | 82 | 60 | 99 | 62 |
| 2[a] | 89 | 83 | 97 | 94 |
| 3[a] | 85 | 82 | 96 | 97 |
| 4[a] | 20 | 15 | 93 | 92 |
| 5[a] | — | — | 90 | 87 |
| 6[b] | — | — | 72 | 18 |
| 7[b] | — | — | 81 | 55 |
| 8[b] | — | — | 27 | 49 |
| 9[a] | 34 | 29 | 89 | 86 |
| 10[b] | — | — | 90 | 92 |
| 11[a] | — | — | 70 | 34 |
| 12[a] | — | — | 86 | 93 |
| 13[c] | — | — | 92 | 88 |
| 14[c] | — | — | 93 | 94 |
| 15 | — | — | 38 | 27 |
| 16 | — | — | 61 | 55 |
| 17[c] | — | — | 79 | 74 |
| 18[b] | — | — | 98 | 15 |
| 19[a] | 56 | 44 | 93 | 87 |
| 30[c] | — | — | 85 | 80 |
| 31[b] | — | — | 99 | 53 |
| 32[a] | 90 | 88 | 67 | 71 |

[a]: auxochrome —OH in para or 1,4
[b]: auxochrome —OH in ortho or 1,2
[c]: auxochrome —NH$_2$ in para

B. *P. Chrysosporium*

Figure 3:
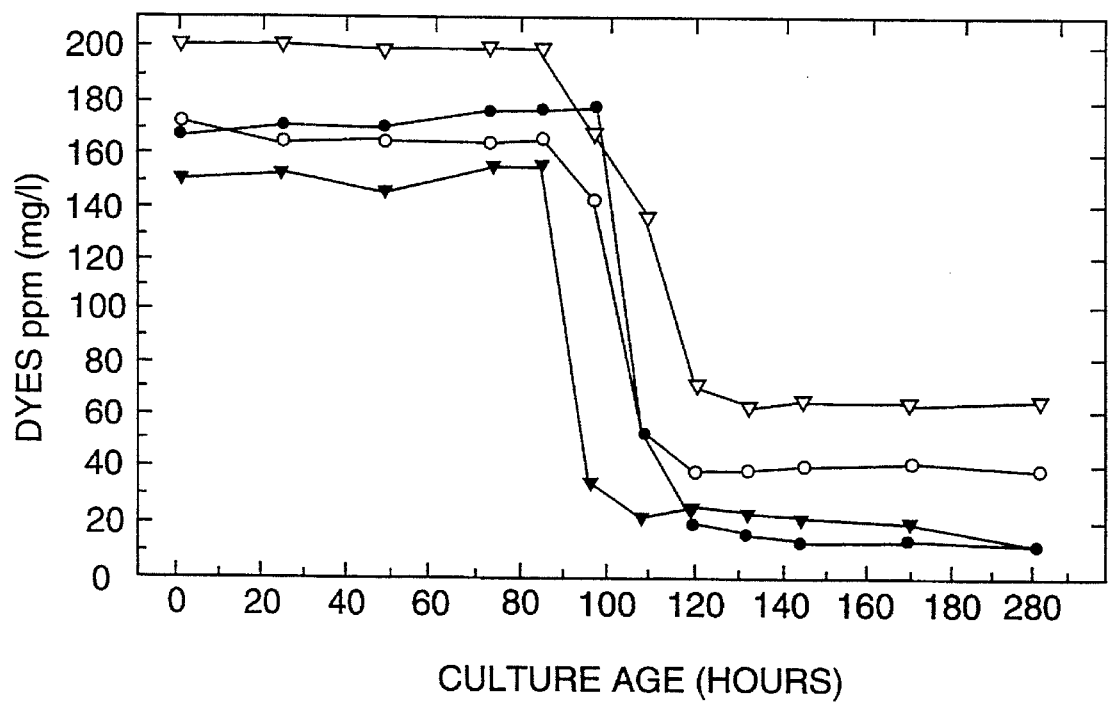
FIG. 3 is a graph showing the rate of degradation by *Phanerochaete chrysosporium* of three azo dyes and sulfanilic acid.

The Phanerochaete fungus almost completely (90%) degraded azo dyes 1 and 2 after a growth period of seven days as shown in FIG. 3. The graph shows decolorization or removal by *P. chrysosporium* of sulfanilic acid (v), acid yellow 9 (O), azo dye 1 (●), and azo dye 2 (▼). Agitated cultures were grown at 37° C. in a mineral medium supplemented with phenylalanine, and starting dye concentrations were 150–200 ppm. There was a characteristic lag of 80–90 hours prior to degradation of any of the compounds by the fungus due to slower growth compared to the Streptomyces. On the solid medium, *P. chrysosporium* behaved similarly leaving some undegraded color after two weeks of growth. *P. chrysosporium* apparently degrades using its ligninolytic enzymes. The ability of this organism to oxidize sulfonated azo aromatic compounds was also tested, shown in FIG. 3 and Table 4. The maximum rate of decolorization occurred on the fourth day of growth in the BII medium for all of the compounds. However, in the cultures with yellow 9 or sulfanilic acid, as assayed by spectrophotometric and HPLC analysis, some undegraded dye remained in the medium after decolorization ended. Yet using HPLC, the inventors were not able to detect any residual substrate in the culture broth after 1 week of growth, even though color was still present in the culture filtrates. One explanation is the finding of Kulla, et al., supra, who found that in cultures of Pseudomonas which were actively degrading azo dyes, secondary oxidative coupling occurred between sulfonated and nonsulfonated phenols, giving dead-end polymers resistant to further degradation.

In testing which, if either, of the ligninolytic peroxidases of *P. chrysosporium* was involved in the degradation of these azo compounds, it was found that ligninase oxidized yellow 9 and sulfanilic acid (FIG. 4A and B), while manganese peroxidase oxidized azo dyes 1 and 2 (FIG. 4C and D). The HPLC analysis of the reaction mixture after incubation of azo dye 1 with manganese peroxidase revealed polymorphic reaction products (FIG. 5B). Oxidation of sulfanilic acid by ligninase produced a purple unstable product, which upon exposure to air precipitated. During a 15-minute incubation period, oxidation of yellow 9 or sulfanilic acid by manganese peroxidase was not detected, nor the oxidation of azo dye 1 or 2 by ligninase. Thus, it is possible that ligninases may cooperate in the degradation of azo dyes 1 and 2. Azo dyes 1 and 2 were decolorized to a greater extent by *P. chrysosporium* than was acid yellow 9 (Table 4). Even greater decolorization was noted during the growth of *S. chromofuscus* A11 (FIG. 2).

These results show that linking a guaiacol molecule into the dye structure increased its susceptibility to degradation. Azo dye structures are typically conjugated multi-unsaturated systems. This makes it possible to change only one fragment of the molecule and yet have the entire conjugated system become accessible to enzymatic attack, particularly with microorganisms like white-rot fungi that use oxidative enzymes that generate cation radicals. This finding has general application for synthesizing more easily biodegradable azo dyes and other recalcitrant compounds in accordance with the present invention.

To further show the effects of lignin-like substitution *P. chrysosporium* was tested with a number of azo dyes. The fungus was able to decolorize all 19 azo dyes tested including the 3 controls. Table 4 shows that the extent of decolorization varies for each dye tested. The controls, azo dyes 1, 2 and 18, were extensively decolorized at both tested concentrations of 50 and 100 ppm. While only 79% of Acid Yellow 9 (dye 17) was degraded, most of the newly synthesized dyes were degraded within the range of from about 85 to about 99% at a dye concentration of 150 ppm (azo dyes 3–6, 8–14, 19, 30 and 31) (Table 4). This enhanced biodegradability was also observed at the higher concentration of 300 ppm. At this concentration, some dyes (azo dyes 7, 12, 19, and 31) apparently began to be toxic for the fungus (Table 4). For cultures of *P. chrysosporium*, the highest decolorization occurs between day 2 and day 5 for all dyes at a dye concentration of 50 ppm. Fungal cultures showed a characteristic decolorization lag phase of 3–4 days. Decolorization was determined spectrophotometrically. HPLC analysis was used to confirm the disappearance of the azo dyes.

XIII. BIOTRANSFORMATION OF AZO DYES 2–19

Table 5 shows the concentrations of azo dyes 2–19 after cultivation with *P. chrysosporium* for ten days on mineral medium. Table 5 clearly shows that the concentration of azo dyes of the present invention are substantially reduced after cultivation with *P. chrysosporium* for a period of ten days. Hence, xenobiotic azo dyes can be modified to have lignin-like substitution patterns, without affecting the dye characteristics of the azo dye, and then degraded by forming a composition comprising *P. chrysosporium* and the azo dye.

TABLE 5

Concentration of Substrates After Ten Days Cultivation with *P. chrysosporium*

| Azo-comp number | Beginning Concentrations | | | |
|---|---|---|---|---|
| | 100 ppm | 150 ppm | 200 ppm | 300 ppm |
| 2 | 2.493 | 6.350 | 10.068 | 7.318 |
| 3 | 0.358 | 1.223 | 1.894 | 114.772 |
| 4 | 1.637 | 3.763 | 4.218 | 16.323 |
| 5 | 6.084 | 9.870 | 14.500 | 22.680 |
| 6 | 12.909 | 14.003 | 33.309 | 39.326 |
| 7 | 62.893 | 41.044 | 10.200 | 246.044 |
| 8 | 16.079 | 28.401 | 29.704 | 135.680 |
| 9 | 81.911 | 109.822 | 32.044 | 153.733 |
| 10 | 8.135 | 15.279 | 46.588 | 42.897 |
| 11 | 6.795 | 14.416 | 30.075 | 21.765 |
| 12 | 2.368 | 44.227 | 6.160 | 198.240 |
| 13 | 7.734 | 20.776 | 28.216 | 20.096 |
| 14 | 4.411 | 11.843 | 15.529 | 36.800 |
| 15 | 1.901 | 10.589 | 17.931 | 17.791 |
| 16 | 67.801 | 92.683 | 179.300 | 219.079 |
| 17 | 29.803 | 58.942 | 93.250 | 136.057 |
| 18 | 8.387 | 20.342 | 40.875 | 77.099 |
| 19 | | | 2.938 | 252.592 |

Table 6 shows the concentration of azo dye substrates after cultivation with Streptomyces strains A10, A11, A12, and A13.

TABLE 6

Percent Degradation of Substrates After Streptomyces Cultivation

| Substrates | Wavelengths | Degradation (%) Strains | | | |
|---|---|---|---|---|---|
| | | A10 | A11 | A12 | A13 |
| 2 | 396 | 77 | 73 | 43 | 18 |
| 3 | 396 | 68 | 73 | 39 | 10 |
| 4 | 416 | 79 | 83 | 39 | 8 |
| 5 | 386 | 9 | 20 | 3 | 8 |
| 6 | 376 | — | — | — | — |
| 7 | 430 | — | — | — | — |
| 8 | 422 | — | — | — | — |
| 9 | 420 | — | — | — | — |
| 10 | 394 | 11 | 16 | 7 | 6 |
| 11 | 420 | 4 | 9 | — | — |
| 12 | 376 | — | — | — | — |
| 13 | 376 | 2 | 5 | 1 | 1 |
| 14 | 466 | — | — | — | — |
| 15 | 474 | 2 | 3 | 1 | 1 |
| 16 | 350 | — | — | — | — |
| 17 | 408 | — | — | — | — |
| 18 | 386 | — | — | — | — |

— = no degradation

The Streptomyces were grown on the same media and under the same conditions as previously described. Spectroscopic analysis of substrates 14, 15, 16, 18 was unaffected by pH over the tested pH range. However, the $Abs_{max}$ of the substrates 1–12 shifts with pH changes. Thus, the spectrophotometric assays for substrates 1–12 were carried out at their specific isobastic points. Degradation was calculated as percent of substrates removed from culture broth, considering the evaporation factor (around 10%). The substrates' concentrations have been calculated versus standard curves prepared for each dye (0–50 μg) at the chosen wavelength; standard curves of the tested concentrations were linears.

Table 6 shows that the concentrations of azo dyes having guaicol-like or syringyl-like substitutions decrease when cultivated with Streptomyces. Hence, xenobiotic azo dyes can be degraded by modifying the dyes to have a lignin-like substitution pattern, such as guiacol-like or syringyl-like, without changing the dye characteristics, and then forming a composition by cultivating the dyes with Streptomyces.

XIV. EFFECT OF VERATRYL ALCOHOL

A. Overview

As shown above, *Phanerochaete chrysosporium* decolorized polyaromatic azo dyes in ligninolytic culture. The oxidation rates of individual dyes depended on their structures. Veratryl alcohol (VA) (3,4-dimethoxy benzyl alcohol) stimulated azo dye oxidation by pure lignin peroxidase (ligninase, LiP) in vitro. Accumulation of compound II of lignin peroxidase, an oxidized form of the enzyme, was observed after short incubations with azo substrates. When veratryl alcohol was also present, only the native form of lignin peroxidase was observed. Azo dyes acted as inhibitors of veratryl alcohol oxidation. After an azo dye had been degraded, the oxidation rates of veratryl alcohol recovered, confirming that these two compounds competed for ligninase during the catalytic cycle. Veratryl alcohol acts as a third substrate (with $H_2O_2$ and the azo dye) in the lignin peroxidase cycle during oxidations of azo dyes.

Veratryl alcohol is a secondary metabolite found in ligninolytic cultures of *Phanerochaete chrysosporium*. Veratryl alcohol is synthesized de novo by way of phenylalanine, 3,4-dimethoxycinnamyl alcohol, and veratryl glycerol. The onset of ligninolytic activity and glucose oxidation leading to hydrogen peroxide production by *P. chrysosporium* appears simultaneously with the accumulation of VA in cultures.

The onset of ligninolytic activity in *Phanerochaete chrysosporium* requires VA, but the relationship between the concentration of VA produced by various strains of *P. chrysosporium* and their mineralization of lignin is not clear. Studies with whole cultures of *P. chrysosporium* indicate that the function of VA might be to protect ligninase against inactivation by hydrogen peroxide. This has been confirmed by experiments where high concentrations of hydrogen peroxide were added to non-protein-synthesizing cultures. The concentration of VA necessary for protection of ligninase activity was in direct proportion to the rate of hydrogen peroxide synthesis by the cultures.

Using pure ligninase preparations, the degradation of the azo dyes by *P. chrysosporium* was investigated. Oxidations of VA and azo compounds were monitored simultaneously since they have considerably different absorption maxima. The results suggested that LiPI (lignin peroxidase compound one), formed during oxidation of $H_2O_2$ by LiP, oxidized polyaromatic azo dyes, forming LiPII. LiPII was then reduced back to the native enzyme by oxidation of VA.

Decolorization of some azo dyes by LiP was almost totally dependent on the presence of VA. VA significantly increased the oxidation rates of these azo dyes. A simultaneous inhibition of LiP-catalyzed VA oxidation by azo compounds was observed. When azo dye oxidations were terminated, the rates of VA oxidation recovered. These observations suggest that LiPI is able to oxidize these dyes, but the LiPII formed requires VA to recycle to the native state. Similar enzymatic oxidation interactions could be involved during degradation of lignin and other recalcitrant compounds.

B. Degradation of Azo Dyes

Decolorization of dyes in cultures were monitored at their absorption maxima at pH 4.5, or using HPLC. A Spherisorb ODS2 C18 column was used for HPLC analysis with a sequence of DMS buffer at pH 4.5 and acetonitrile as solvents (5 min 100% DMS, 15 min 100% acetonitrile, 18 min 100% acetonitrile, 19 min 100% DMS, 20 min 100% DMS, 5 min postran 100% DMS). Peaks were monitored at 260 and 450 nm. Results from spectrophotometric and HPLC methods were compared.

C. Enzyme Assays

Lignin peroxidase activity was determined spectrophotometrically at room temperature with VA as substrate. One unit (U) of enzyme activity was defined as 1 μmole of veratryl aldehyde formed-per-min at pH 3. Simultaneous oxidations of azo dyes and veratryl alcohol were measured using a Hewlett-Packard 8452 diode array spectrophotometer operated in the kinetic mode by a Vectra PC equipped with MS™-DO/UV-VIS software. Azo dye concentrations were determined by measuring absorbances at appropriate maxima. Dye 24 shows $E_{(506)}=5.07\times10^4 M^{-1}\,cm^{-1}$, and dye 28 shows $E_{(430)}=4.12\times10^4 M^{-1}\,cm^{-1}$.

Table 7 shows the decolorization of individual azo dyes by a ligninolytic culture of *P. chrysosporium* after ten days of growth. The initial concentration of dye was 200 mg-per-liter. Numbers represent mg-per-liter of dye remaining in the cultures.

TABLE 7

| | Analytic Methods | | |
|---|---|---|---|
| Azo Dye | HPLC | Spectrophotometry | Amount Degraded (av. %) |
| 20 | 62.20 | 52.01 | 71.45 |
| 21 | 103.62 | 102.38 | 48.50 |
| 22 | 12.28 | 7.64 | 95.02 |
| 23 | 72.43 | 89.27 | 59.57 |
| 24 | 4.43 | 1.11 | 98.61 |
| 25 | 14.86 | 9.66 | 93.87 |
| 26 | 6.98 | 4.33 | 97.17 |
| 27 | 29.42 | 28.33 | 85.56 |
| 28 | 3.00 | 2.42 | 98.64 |
| 29 | 109.39 | 108.92 | 45.42 |

— Dyes 20 to 26 contain naphthalene.
— Cultures with dyes 24 and 28 were completely bleached.

D. Enzyme Purification

After six days of growth, when the specific activity of ligninase reached about 250 U-per-liter, culture filtrates were separated from mycelial debris by filtration. One liter of culture filtrate was concentrated to about 10 ml using an Amicon PM-10 membrane and desalted in 10 mM sodium acetate buffer (pH 6) using a Sephadex G25 NAP10 column. Ligninase isoenzyme was separated from Mn-dependent peroxidases using a Pharmacia fast protein liquid chromatography system equipped with a Mono Q HR 5/5 column. In this study isoforms H2 and H8 were used. The purified proteins were electrophoretically homogenous and showed $A_{408}/A_{280}$ of about 4.5.

E. Oxidation of Azo Dyes

Figure 7A:
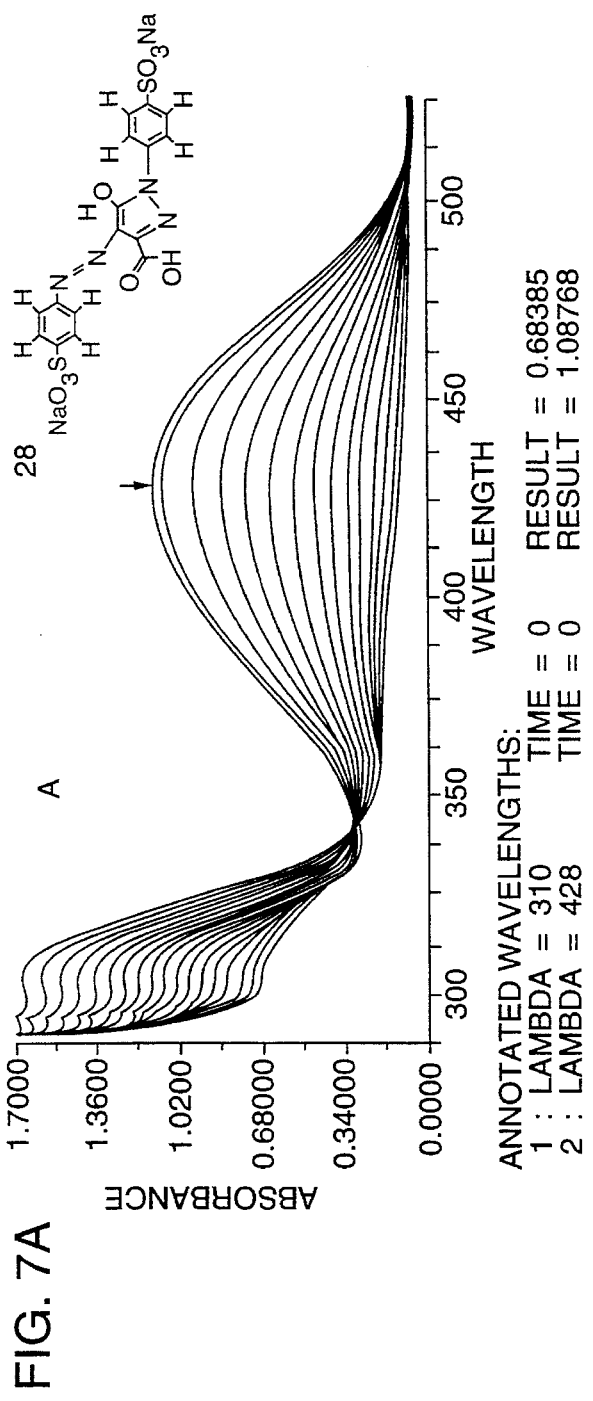
FIG. 7A shows the oxidation of veratryl alcohol and azo dye 28 by lignin peroxidase.
Figure 7B:
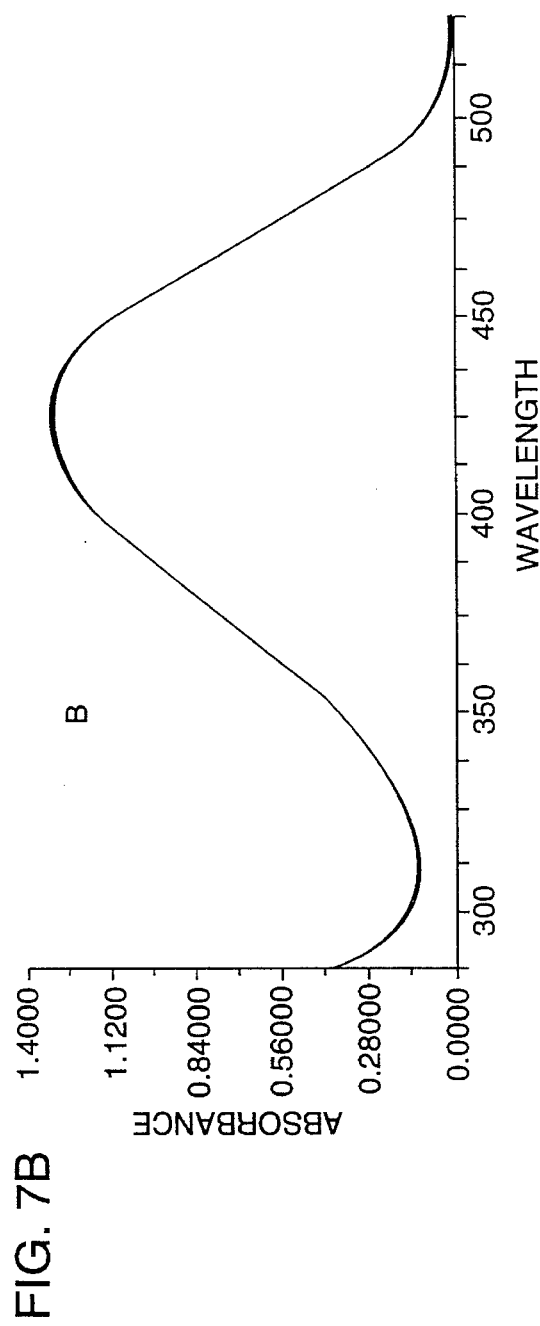
FIG. 7B shows the oxidation of azo dye 28 in the absence of veratryl alcohol.

In vitro studies were limited to dyes 24 and 28. Ligninase without VA oxidized azo dyes 24 and 28 to a limited extent. After VA was added to the reaction mixtures, oxidation of both substrates began, leading to total decolorization of the dyes. FIGS. 6A and 7A show the simultaneous oxidation of azo dyes 24 and 28, respectively, and VA by ligninase. Without VA, azo dye oxidation was limited and terminated more rapidly than in the presence of VA (FIGS. 6B and 7B). When a dye was present in a reaction mixture, the rate of VA oxidation decreased due to an apparent competition for LiPI between these two compounds. The oxidation rate of VA recovered when the azo dye oxidation was completed (FIG. 8). The maximal rate of VA oxidation was about 159 AU (absorption change per-min-per-ml of ligninase solution). Wavelengths of 310 nm for VA, 506 nm for dye 24, and 430 nm for dye 28 oxidations were used in monitoring substrate removal. The oxidation of azo dyes is stimulated by VA in high (200 μM) and low (20 μM) $H_2O_2$ concentrations. These results establish that ligninase is capable of more effectively oxidizing recalcitrant azo dyes when VA is present.

Figure 9:
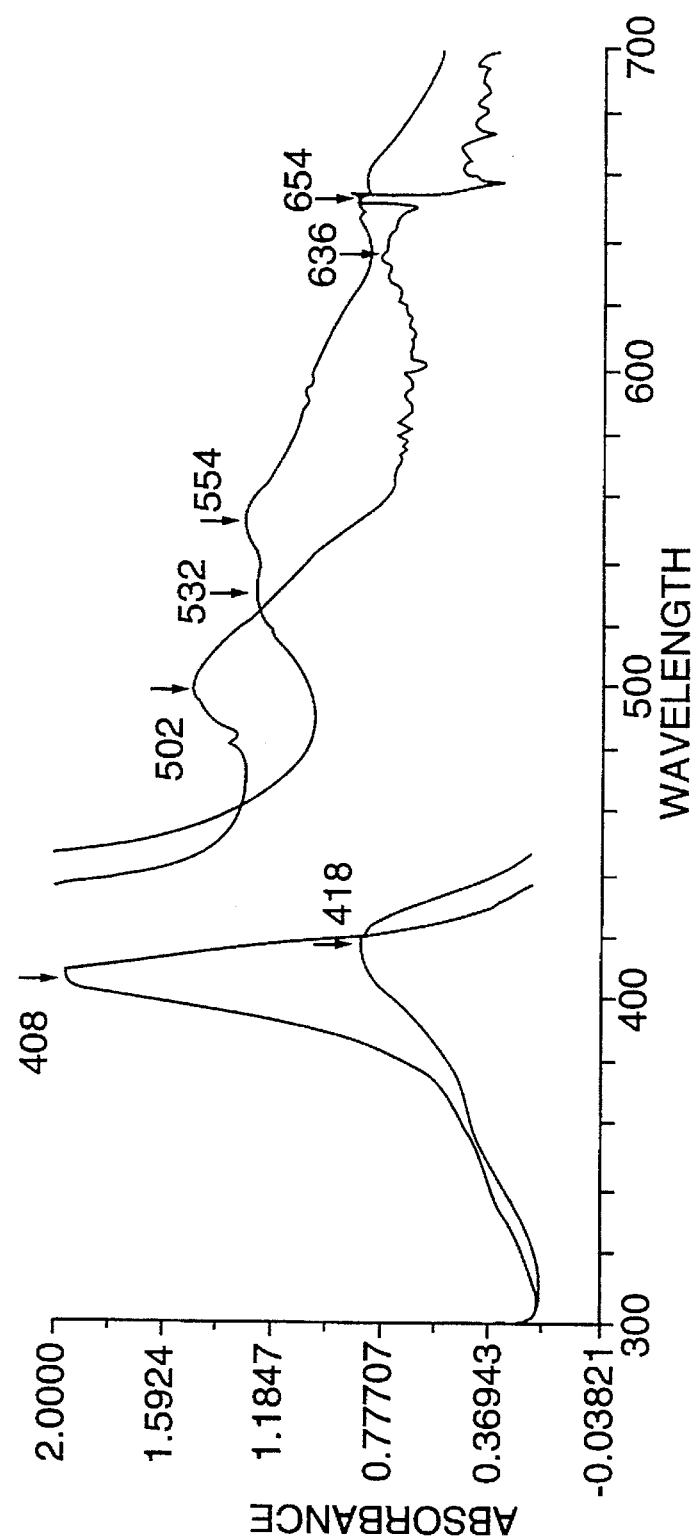
FIG. 9 shows the absorption rate of ligninase in the reaction mixture with veratryl alcohol.

Ligninases from two parallel reaction mixtures were recovered by Sephadex G25 gel filtration, and spectra were recorded (FIG. 9). The first reaction mixture contained 50 mM sodium tartrate at pH 3, 18 μM enzyme, 0.2 mM $H_2O_2$, 15 μg of dye 28, and 1 mM VA. In the second reaction mixture, VA was excluded. Spectrum were observed of the native enzyme in the reaction mixture that had contained VA, and the spectrum of LiPII in the reaction mixture that had not contained VA, in which only the azo dye was available as a reductant. Dyes 24 and 28 gave similar results. Without limitation it appears that only the highest oxidation stage of ligninase (LiPI) is able to attack azo dyes, and that the presence of VA helps to complete the catalytic cycle of the enzyme.

XV. MINERALIZATION OF AZO DYES BY *P. CHRYSOSPORIUM* AND *STREPTOMYCES CHROMOFUSCUS*

A. Measurement of the Mineralization of [$^{14}$C]-Labeled Dyes

Agitated cultures containing 100,000 to 150,000 dpm of azo dye at a concentration of 200 mg/liter for *P. chrysosporium* and 50 mg/liter for *S. chromofuscus* were incubated at 37° C. for 20 days with shaking at 200 rpm. For each mineralization experiment six replicates-per-culture were run for *P. chrysosporium* and three replicates-per-culture for *S. chromofuscus*. Each culture flask contained a $CO_2$ trap consisting of a small glass cup connected to the bottom of the rubber stopper. The cup contained 1 ml of 1N NaOH. Samples were taken every 2 days, and after each sampling cultures were flushed with 100% oxygen for 30 s. At the sampling time, the stopper was removed and the NaOH containing trapped $CO_2$ was transferred to a 20-ml scintillation vial, and the cup was then rinsed twice with 1 ml of water. Two ml of rinse water were also transferred to the vial. Finally, 10 ml of Ecolite scintillation cocktail (ICN Biochemicals Inc., Irvine, Calif.) were added to each vial. Vials, after mixing, were stored in the dark for 24 h. The cpm of trapped radioactivity was then determined in a Packard Tri-Carb liquid scintillation analyzer, Model 1500, using the $^{14}$C quench standards and SIS numbers.

B. Measurement of Organic Volatile Compounds

Either a charcoal-containing polyurethane sponge (Bio-Rad Laboratories, Richmond, Calif.) or 2-methoxyethanol was used to trap volatile organic compounds released during mineralization experiments. The sponge (1 cm$^3$) replaced the 1N NaOH solution in the small glass cap attached to the rubber stopper; other conditions were as before for the $^{14}CO_2$ experiments. For scintillation counting, the charcoal sponges were dissolved in 1 ml of hyamine hydroxide contained in scintillation vials (1M solution in methanol; NEN Research Products, Boston, Mass.) held at 55° C. for 2 h. Ten ml of Ecolite scintillation cocktail were then added and the cpm was measured.

In the second procedure, cultures with $CO_2$ traps were flushed with oxygen for 10 min, and the organic volatiles present were trapped in 10 ml of 2-methoxyethanol mixed with 10 ml Ecolite.

C. Radioactivity in the Medium and Biomass

The removal of radioactivity from the media was determined by measuring the amount of $^{14}C$ label in 0.1 ml of the medium at time 0 and 21 days for each culture. Uninoculated cultures were used as evaporation controls. At the end of each mineralization experiment, culture broths were used as evaporation controls. At the end of each mineralization experiment, culture broths were acidified with 5 ml of 1M $H_3PO_4$, fresh 1N NaOH was added to the trap, and the cultures were shaken overnight. No additional releases of $^{14}CO_2$ were observed. The radioactivity assimilated by the cells was measured by solubilizing biomass harvested from each 21-day-old culture in an equal volume of hyamine hydroxide solution. Before solubilization, cells were washed three times with 50 ml of distilled water to remove adsorbed dyes. Ecolite 10 ml was added to the mixture, which was vortexed vigorously. To increase counting efficiency, the solution of biomass-hyamine-scintillation cocktail was further diluted 10 to 20 times with fresh Ecolite before counting.

*P. chrysosporium* demonstrated a greater ability than *Streptomyces chromofuscus* to mineralize the azo dyes. *S. chromofuscus* mineralized certain dyes which is significant, since azo dyes are resistant to aerobic degradation. About 19% of the radioactivity from guaiacol-substituted azo dye 34 was removed from the medium after 21 days growth of *S. chromofuscus*. Of this amount, almost 4% of the $^{14}C$ was mineralized to $CO_2$ and 4.6% was assimilated by the cells of the actinomycete. Since the dyes were at least 99% radiochemically pure, the recovered $^{14}C$ in $CO_2$ and biomass must represent mineralized dye molecules. The remaining 9% of the radioactivity was accounted for by dye absorbed by the cells. Dyes 35 and 37 showed similar patterns of degradation, although mineralization was less efficient. *P. chrysosporium* assimilated similar ranges of degraded dyes and showed smaller amounts of absorption to cell mass, with the exception of sulfanilic acid.

Two methods were used to detect the production of organic volatiles. Polyurethane foam containing activated charcoal was a less-sensitive trap than the 2-methoxyethanol purging method. After solubilization, the foam released activated charcoal, which caused quenching problems during the counting of radioactivity. By using 2-methoxyethanol as the trapping agent, small but measurable amounts of $^{14}C$ released by the cultures of *P. chrysosporium* were detected.

The benzene ring that is attached directly to the azo linkage and that has the sulfonic group in the para position is the most recalcitrant portion of the azo dye molecule. This benzene ring was radiolabeled since this moiety was common to all the investigated compounds, and therefore the results of the degradation and mineralization experiments were comparable. In all cases the guaiacol moiety retained its full electronic configuration since it is attached to a remote part of the molecule.

*S. Chromofuscus* mineralized azo dyes only when the lignin-like guaiacol structure was attached to the sulfonated aromatic ring. The results of the mineralization experiments with *P. chrysosporium* (Table 8) showed less of a pattern. It appears that the bacterial enzymatic system responsible for the degradation are more specific to lignin-like structures than are the enzymatic system(s) of the fungus.

TABLE 8

Percentage of radioactivity recovered in $CO_2$ and biomass and the percentage of radioactivity removed from the medium after 21 days' growth of *P chrysosporium* and Streptomyces A11

| | P. chrysosporium | | | Streptomyces chromofuscus | | |
|---|---|---|---|---|---|---|
| Azo dye | Medium** | $CO_2$ | cells | Medium | $CO_2$ | cells |
| 3 | 31.7 | 25.7 | 5.2 | 19.0 | 3.6 | 4.6 |
| 17 (Acid Yellow 9) | 33.0 | 26.9 | 2.3 | 0.0 | 0.0 | 0.0 |
| 19 | 41.6 | 34.8 | 2.3 | 0.0 | 0.0 | 0.0 |
| 31 (Orange II) | | | | | | |
| 32 (Orange I) | 29.6 | 19.7 | 4.0 | 22.0 | 1.1 | 7.0 |
| Sulfanilic Acid | 25.0 | 17.2 | 1.3 | 0.0 | 0.0 | 0.0 |

*In addition to $CO_2$, a small amount (0.1%–0.5%) of organic volatiles were detected.
**C not accounted for as $CO_2$ or biomass was lost by absorption to cell material and could be removed by washing with distilled water.

Figure 11:
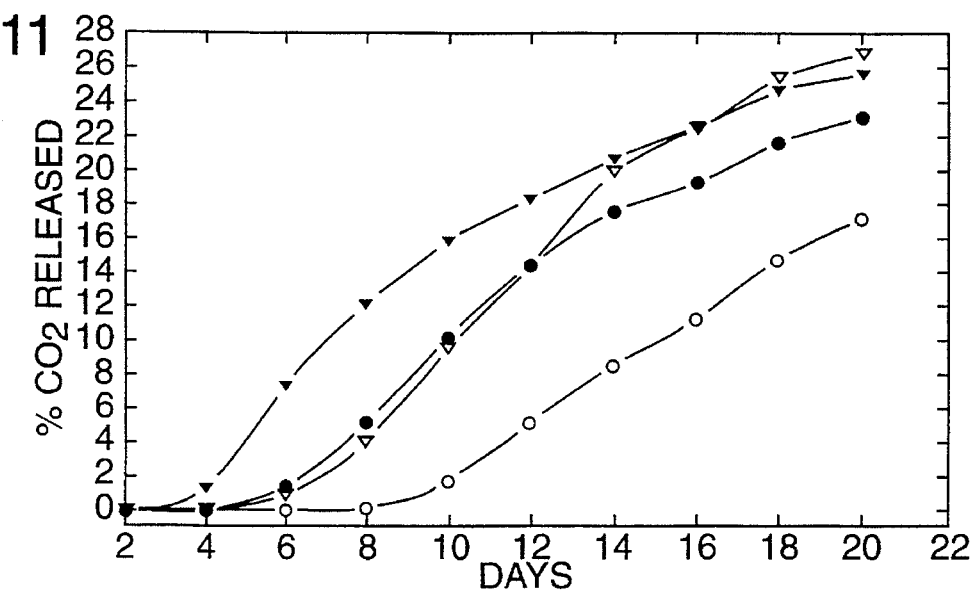
FIG. 11 shows the percent of $^{14}CO_2$ released versus time for the mineralization of sulfanilic acid and azo dyes 33, 34, and 35 by shaken cultures of *P. chrysosporium*.
Figure 12:
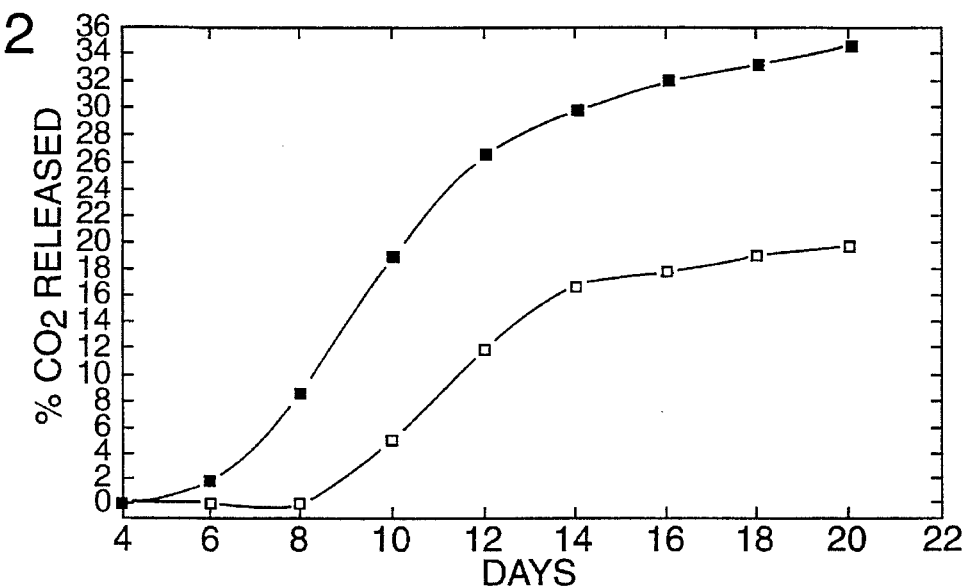
FIG. 12 is a graph showing the percent of $^{14}CO_2$ released versus time for the mineralization of azo dyes 36 and 37 by shaken cultures of *P. chrysosporium*.
Figure 13:
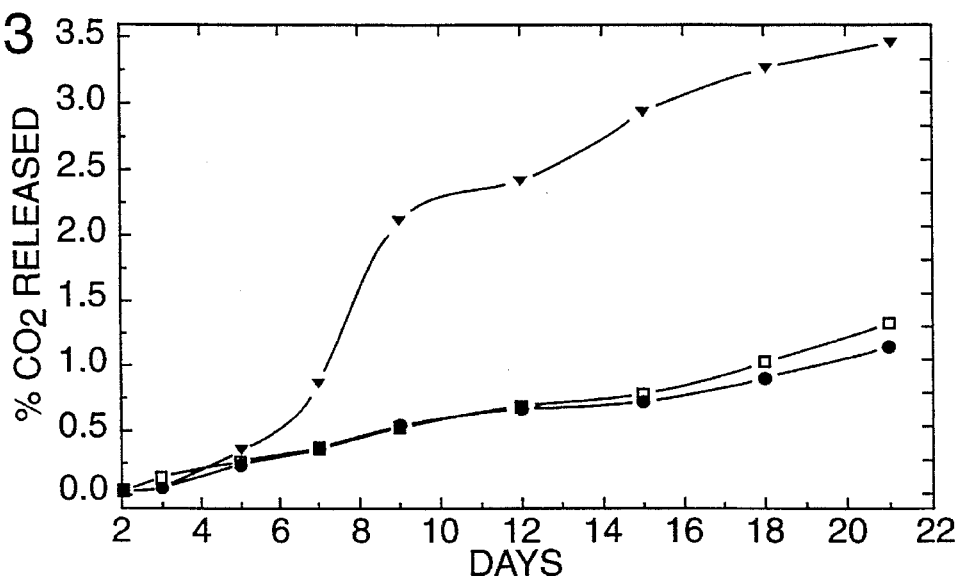
FIG. 13 is a graph showing the percent of $^{14}CO_2$ released versus time for the mineralization of azo dyes 34, 35 and 37 by shaken cultures of *S. chromofuscus*.

Mineralization experiments were conducted with both organisms to determine how structural variations in the second ring of the azo dyes affected degradation rates over a 21-day incubation period. A progressive mineralization of each azo dye was observed (FIGS. 11–13). With *P. chrysosporium,* dye 36 was degraded 2.5 times greater than the dye 37, and degradation began 2 days earlier. Dyes 33, 34, and 35 were mineralized to a similar extent, although the mineralization rate of dye 34 was twice as fast during the first 10 days of incubation. The streptomycetes mineralized only the guaiacol derivatives of dyes 34 and 35. A significant increase in the mineralization rate of dye 34 could be observed between days 6 and 9. The mineralization of sulfanilic acid (FIG. 12) began on the tenth day of the fungal culture and reached only 17%. During mineralization, a brown oxidation product accumulated at the beginning of degradation (14 days). This product was subsequently bleached by the culture. This brown material was probably a product of the oxidative coupling of benzene-carrying hydroxy and amino groups.

Both *P. chrysosporium* and streptomycetes mineralize sulfonated azo dyes, including naphthol derivatives, which make up the bulk of commercial dyes. Since actinomycetes and fungi are able to decolorize and mineralize azo dyes, such compounds can be used as assay compounds to isolate superior catabolic microbial strains from natural environments. Peroxidases seem to perform an essential role in azo dye transformations.

XVI. DEGRADATION OF AZO DYES BY SOIL MICROFLORA

Azo dyes according to the present invention also can be degraded by forming a mixture of the azo dye and soil or soil microflora other than *Phanerochaete chrysosporium* and Streptomyces spp.

The degradation of azo dyes by soil microflora in general was evaluated by forming a mixture of azo dyes 33 and 34 with water from a soil sample. The soil sample contained soil microflora that had not adapted to using azo dyes as substrates. A carbon source was added to the mixture and a continuous air flow through the mixture was maintained. The $^{14}CO_2$ released by the mixture was trapped using a 1N NaOH.

The results of this study showed that soil microflora other than *Phanerochaete chrysosporium* and Streptomyces spp. are capable of degrading azo dyes. Furthermore, attaching a lignin-like substituent to the azo dye enhances the degradation of the dye. Specifically, azo dye 33 was transformed only 3.4% and mineralized only 1.1% when combined with water from a soil sample. Azo dye 34, having a guaiacol substitution pattern, was degraded much more effectively, since 46% of the dye was transformed, and 14% of the dye was mineralized.

XVII. Lignin-Like Structures

As the data in Tables 1–8 demonstrate, the biodegradability of xenobiotics, such as azo dyes, can be enhanced by attaching lignin-like structures to them. Lignin-like structures are those that are contained in lignin and which enhance biodegradability of xenobiotic azo dyes when they are attached to them. Lignin-like structures also include analogous chemical structures which are not known to be in lignin, yet sufficiently resemble lignin structures to provide enhanced biodegradability.

Chemical and spectrometric studies of softwood lignin indicate that lignin is an aromatic polymer in which the monomeric guaiacylpropane units are connected by both ether and carbon-carbon linkages. Several substructures in lignin macro-molecules include guaiacylglycerol-β-aryl ether (β-O-4' substructure 1) which is the most abundant interphenylpropane linkage (40–60%) in lignin, followed by phenylcoumaran (β-5' substructure 2; 10%), diarylpropane (β-1' substructure 3; 5–10%), pinoresinol (β-β' substructure 4; 5%), biphenyl (5-5' substructure 5; 10%), diphenyl ether (4-O-5' substructure 6; 5%), and others.

A structure model of softwood lignin is described in Higuchi, *Biosynthesis and Biodegradation of Wood Components*, Wood Research Institute, Kyoto, Japan, 1985, page 143, and set forth below to show a variety of ring substitutions present in lignin.

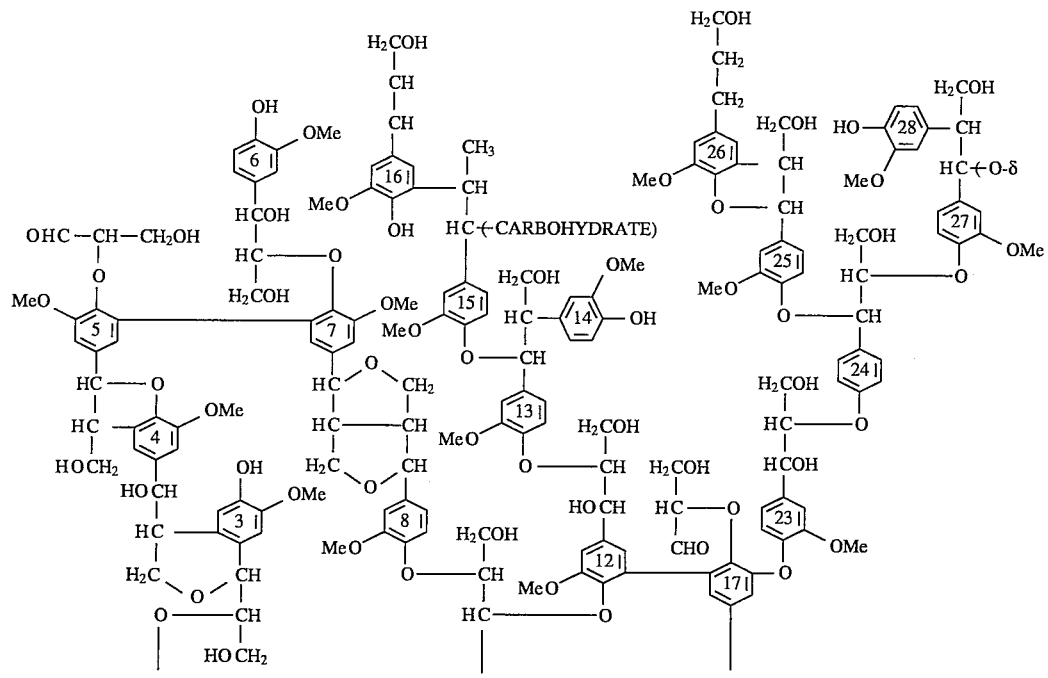

-continued

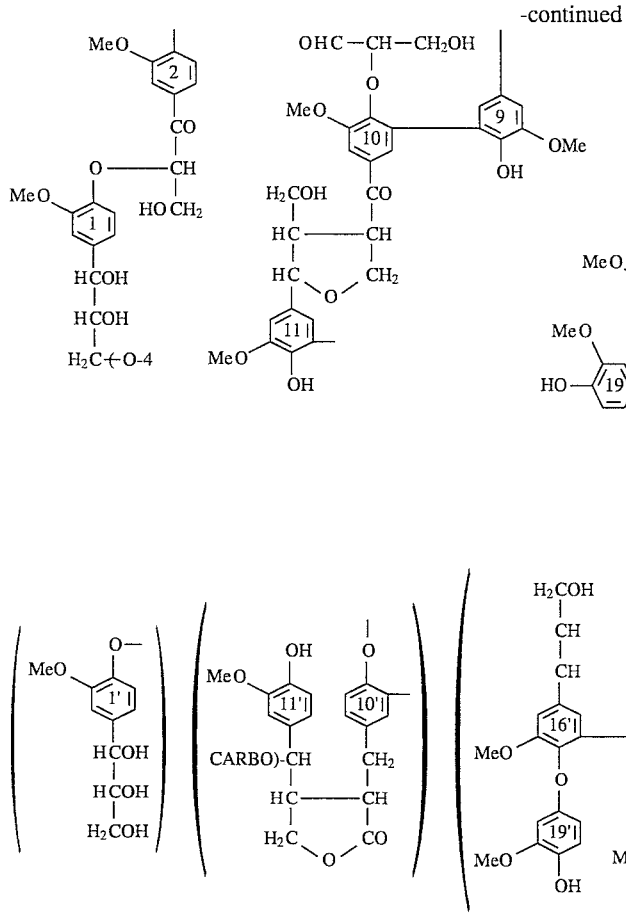
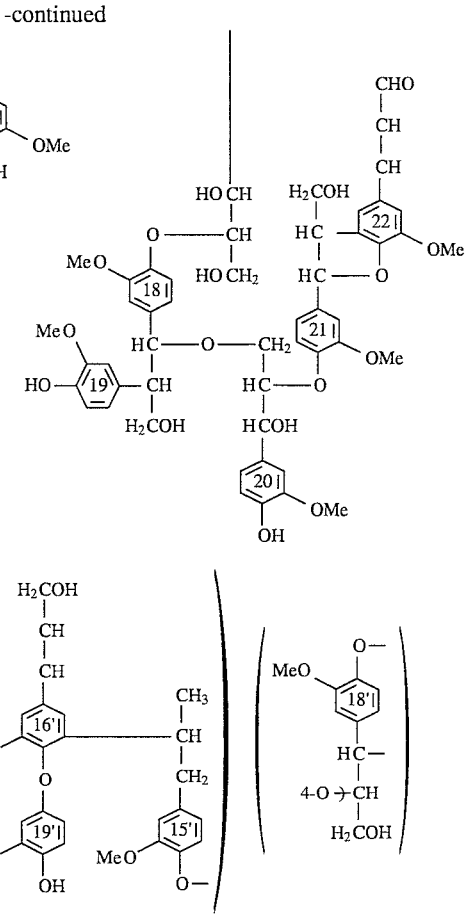

The composition of lignin varies for different kinds of lignins. The lignin of hardwoods such as beech, for example, is composed of approximately equal amounts of guaiacyl- and syringylpropane units connected by linkages similar to those found in spruce lignin. Grass lignin, such as bamboo lignin, is considered to be composed of guaiacyl-, syringyl-, and p-hydroxyphenyl.

The biodegradable azo dyes of the present invention include an azo group having a nitrogen atom linked to an aromatic ring, in which the ring has a lignin-like substitution pattern. As used herein, the term "lignin-like substitution pattern" refers to a ring having substituents which provide a lignin-like structure. In its simplest embodiments, the lignin-like substitution pattern provides guaiacyl-like or syringyl-like units connected by a nitrogen linkage to the remainder of the azo dye. Guiacol-like as used herein means, without limitation, that the azo dye has a hydroxy group or lower alkoxy group on at least one aromatic ring with an electron releasing group, such as a lower alkyl or lower alkoxy group, ortho to the hydroxy group. Preferred guiacol substitution patterns have the hydroxy group para to the azo group. Especially preferred guaicol-like substitution patterns have the hydroxy group para to the azo group with the electron-releasing group, comprising methyl or methoxy, ortho to the hydroxy group. The aromatic ring can comprise naphthalene, wherein the second aromatic ring of the naphthalene system acts as an electron-releasing group. Syringyl-like as used herein means, without limitation, that the azo dye has a hydroxy group or lower alkoxy group on at least one aromatic ring and two electron releasing groups, such as a lower alkyl, lower alkoxy, or lower alkyl and lower alkoxy, ortho to the hydroxy group. Preferred syringyl-like substitution patterns have the hydroxy group para to the azo group. Especially preferred syringyl-like substitution patterns have the hydroxy group para to the azo group with the electron-releasing groups, comprising methyl, methoxy, or methyl and methoxy, ortho to the hydroxy group. The aromatic ring can comprise naphthalene wherein the second aromatic ring of the naphthalene system acts as an electron-releasing group.

XVIII. SUMMARY

The present inventors have found that biodegradability of azo dyes is especially enhanced by providing a lignin-like substitution pattern on one of the aromatic rings of the azo dye. The lignin-like substitution pattern may comprise a first ring substituent R1 selected from the group consisting of hydroxy, lower alkoxy or amino, and a second substituent R2 selected from the group consisting of lower alkyl, lower alkoxy and halogen. In especially preferred embodiments, a third ring substituent R3 is selected from the group consisting of lower alkyl, lower alkoxy and halogen.

It is preferred, although not necessary, that the azo dye be a fully conjugated system. In particular embodiments, the dye includes a plurality of azo groups having nitrogen atoms linked to aromatic rings such that the compound is a fully conjugated system. Diazo or triazo compounds, for example, would provide such a fully conjugated system. Such fully conjugated systems are both brighter and more susceptible to degradation. However, some less than fully conjugated dyes (such as C.I. 25380 direct red 75; C.I. 29156 direct orange 102; C.I. 29160 direct red 23; and C.I. 13950 direct yellow 27) may also be modified by adding lignin-like moieties to make them more biodegradable. Modification of a portion of the dye molecule will at least make that part of the molecule more degradable, and may as a result make the entire molecule more degradable.

The aromatic ring having the lignin-like substitution pattern can be phenyl, naphthyl or other aromatic structures. A naphthyl ring is shown in azo dyes 19–26, 31, 32, 36, and 37. The dye may preferably include a sulfonic acid group to increase solubility of the dye. The sulfonic acid group may be present on either the lignin-like ring or elsewhere in the molecule.

In particular embodiments, R2 is ortho to R1. In other embodiments, R1 is hydroxy while R2 is a lower alkoxy, such as methoxy, or a lower alkyl group such as methyl or ethyl. In preferred embodiments wherein R1 is hydroxy, R2 may preferably be halogen, such as fluorine or chlorine.

The azo dyes of the present invention preferably include at least one sulfonic acid group, on either the lignin-like ring or somewhere else in the molecule, to increase the solubility of the azo compound. This solubility is important to some dye applications.

In those embodiments in which R2 is ortho to R1, R2 may preferably be lower alkyl, lower alkoxy or halogen.

The present invention provides a composition that includes *Phanerochaete chrysosporium* and azo dyes according to the present invention. Several embodiments of the dyes are degraded by *Phanerochaete chrysosporium*. These embodiments include 4-dimethylamino-azobenzene-4'-sulfonic acid, 4-diethylamino-azobenzene-4'sulfonic acid, 3-methyl-4-hydroxy-azobenzene-4'-sulfonic acid, 3-methoxy-4-hydroxy-azobenzene-4'-sulfonic acid, 3-chloro-4-hydroxy-azobenzene-4'-sulfonic acid, 3-sec-butyl-4-hydroxy-azobenzene-4'-sulfonic acid, 3,5-dimethoxy-4-hydroxy-azobenzene-4'-sulfonic acid, 3,5-difluoro-4-hydroxy-azobenzene-4-sulfonic acid, 3,5-dimethyl-4-hydroxy-azobenzene-4'-sulfonic acid, 2-hydroxy-4,5-dimethyl-azobenzene-4'-sulfonic acid, 2-hydroxy-3-methoxy-5-methyl-azobenzene-4'-sulfonic acid, and 4-(3-methoxy-4-hydroxyphenylazo)-azobenzene-3,4'-disulfonic acid.

Several embodiments of the invention have been found to be particularly suitable for significant degradation by Phanerochaete. These embodiments include the following azo dyes: 4-dimethylamino-azobenzene-4'-sulfonic acid, 4-diethylamino-azobenzene-4'-sulfonic acid, 3-methyl-4-hydroxy-azobenzene-4'-sulfonic acid, 3-methoxy-4-hydroxy-azobenzene-4'-sulfonic acid, 3-chloro-4-hydroxy-azobenzene-4'-sulfonic acid, 3-sec-butyl-4-hydroxy-azobenzene-4'-sulfonic acid, 2-hydroxy-5-methyl-azobenzene-4'-sulfonic acid, 2-hydroxy-5-ethyl-azobenzene-4'-sulfonic acid, 3,5-dimethyl-4-hydroxy-azobenzene-4'-sulfonic acid, 3,5-dimethoxy-4-hydroxy-azobenzene-4'-sulfonic acid, 3,5-difluoro-4-hydroxy-azobenzene-4'-sulfonic acid, 2-hydroxy-4,5-dimethyl-azobenzene-4'-sulfonic acid, 2-hydroxy-3-methoxy-5-methyl-azobenzene-4'-sulfonic acid.

Several embodiments of the invention have been found to be suitable for significant degradation by Phanerochaete when the concentration of the azo dye is less than about 150 ppm. These embodiments of the azo dyes include 4-dimethylamino-azobenzene-4'-sulfonic acid, 4-diethylamino-azobenzene-4'sulfonic acid, 3-methyl-4-hydroxy-azobenzene-4'-sulfonic acid, 3-methoxy-4-hydroxy-azobenzene-4'-sulfonic acid, 3-chloro-4-hydroxy-azobenzene-4'-sulfonic acid, 3-sec-butyl-4-hydroxy-azobenzene-4'-sulfonic acid, 3,5-dimethoxy-4-hydroxy-azobenzene-4'-sulfonic acid, 3,5-difluoro-4-hydroxy-azobenzene-4-sulfonic acid, 3,5-dim-ethyl-4-hydroxy-azobenzene-4'-sulfonic acid, 2-hydroxy-4,5-dimethyl-azobenzene-4'-sulfonic acid, 2-hydroxy-3-methoxy-5-methyl-azobenzene-4'-sulfonic acid, 4-(3-methoxy-4-hydroxyphenylazo)-azobenzene-3,4'-disulfonic acid, 2-hydroxy-5-ethyl-azobenzene-4'-sulfonic acid, 3,4-dimethoxy-azobenzene-4'-sulfonic acid, 1-(4'-benzenesulfoncic acid)-4-hydroxynaphthalene, 4-methoxy-azobenzene-4'-sulfonic acid, 4-amino-1,1'-azobenzene-3,4'-disulfonic acid, 1-phenylazo-2-hydroxynaphthalene-6-sulfonic acid, 4-aminoazobenzene-4'-sulfonic acid and 4-hydroxy-azobenzene-4'-sulfonic acid.

Particularly suitable compositions according to the present invention include *Phanerochaete chrysosporium* and the following embodiments of the azo dyes: 3-methyl-4-hydroxy-azobenzene-4'-sulfonic acid, 3-methoxy-4-hydroxy-azobenzene-4'-sulfonic acid, 3-sec-butyl-4-hydroxy-azobenzene-4'-sulfonic acid, 3,5-dimethoxy-4-hydroxy-azobenzene-4'-sulfonic acid, 3,5-dimethyl-4-hydroxy-azobenzene-4'-sulfonic acid, 2-hydroxy-4,5-dimethyl-azobenzene-4'-sulfonic acid, 2-hydroxy-3-methoxy-5-methyl-azobenzene-4'-sulfonic acid, 4-(3-methoxy-4-hydroxyphenylazo)-azobenzene-3,4'-disulfonic acid, 2-hydroxy-5-ethyl-azobenzene-4'-sulfonic acid, 3,4-dimethoxy-azobenzene-4'-sulfonic acid, and 1-(4'-benzenesulfoncic acid)-4-hydroxynaphthalene.

Compositions according to the present invention can include Streptomyces as the microbe. Where Streptomyces is the microbe, suitable embodiments of the azo dyes include 4-(3-methoxy-4-hydroxyphenylazo)-azobenzene-3,4'-disulfonic acid, 3-methoxy-4-hydroxy-azobenzene-4'-sulfonic acid, and 2-hydroxy-5-ethyl-azobenzene-4'-sulfonic acid.

Compositions according to the present invention having Streptomyces as the microbe may include azo dyes having a third ring substituent $R_3$ selected from the group consisting of lower alkyl and lower alkoxy. $R_2$ and $R_3$ may both be ortho to $R_1$. Suitable embodiments of the azo dyes having both $R_2$ and $R_3$ include 3,5-dimethyl-4-hydroxy-azobenzene-4'-sulfonic acid and 3,5-dimethoxy-4-hydroxy-azobenzene-4'-sulfonic acid.

Particularly suitable azo dye compounds comprise an azo group having first and second nitrogen atoms linked to first and second aromatic rings, wherein the first aromatic ring has a first substituent $R_1$ selected from the group consisting of hydroxy and lower alkoxy, a second substituent $R_2$ selected from the group consisting of lower alkyl, lower alkoxy and fluorine, and a lower alkoxy substituent $R_3$.

The present invention also provides a biodegradable composition comprising (1) an azo dye having first and second nitrogen atoms linked to first and second aromatic rings, the first ring having a lignin-like substitution pattern, (2) an amount of lignin peroxidase effective to degrade said dye, wherein lignin peroxidase is converted to lignin peroxidase II as the dye is degraded, and (3) an amount of veratryl alcohol effective to recycle lignin peroxidase II to lignin peroxidase. An effective amount of lignin peroxidase is defined to mean an amount sufficient to oxidize the azo dye to an oxidized state. An amount of veratryl alcohol effective to recycle lignin peroxidase to lignin peroxidase II is suitably, for example, at least 20 micromoles, and can be 200 micromoles or greater. The lignin peroxidase may be provided by a microbe.

The composition may also comprise an azo dye having first and second nitrogen atoms linked to first and second aromatic rings, and an amount of peroxidase effective to degrade the dye. The peroxidase may be provided by a microbe such as Streptomyces or a fungus such as *Phan-*

*erochaete chrysosporium.* Particularly suitable azo dyes have a hydroxy group para to the first and second nitrogen atoms comprising the azo group.

Azo dyes for the composition may have the first ring include a first substituent $R_1$ selected from the group consisting of hydroxy, alkoxy and amino, and a second substituent $R_2$ selected from the group consisting of hydrogen, lower alkoxy, lower alkyl and halogen. The first aromatic ring may also have a first substituent $R_1$ selected from the group consisting of hydroxy, lower alkoxy, or amino, and a second substituent $R_2$ selected from the group consisting of lower alkyl, lower alkoxy and halogen. The first aromatic ring may have a third ring substituent $R_3$ selected from the group consisting of lower alkyl, lower alkoxy, and halogen.

The azo dye may further comprise a plurality of azo groups having nitrogen atoms linked to aromatic rings such that the compound is a fully conjugated system. Finally, the first aromatic ring may have a first substituent $R_1$ selected from the group consisting of hydroxy and lower alkoxy, a second substituent $R_2$ selected from the group consisting of lower alkyl, lower alkoxy and fluorine, and a lower alkoxy substituent $R_3$.

The present invention also provides a method for degrading xenobiotic azo dyes having first and second nitrogen atoms linked to first and second aromatic rings, the method comprising the steps of (1) providing a lignin-like substitution pattern on the first aromatic ring, and (2) exposing the mixture to an amount of lignin peroxidase effective to degrade the azo dye, wherein lignin peroxidase is converted to lignin peroxidase II as the dye is degraded. The lignin peroxidase may be provided by a microbe, such as *P. chrysosporium*. The method may also include the step of combining veratryl alcohol with the azo dye to form a mixture and exposing the mixture to lignin peroxidase, wherein the veratryl alcohol is added in an amount sufficient to convert lignin peroxidase II to lignin peroxidase.

In a particular embodiment, the biodegradable dye compound comprises an azo group having first and second nitrogen atoms linked to first and second aromatic rings wherein the first aromatic ring has a first substituent $R_1$ selected from the group consisting of hydroxy and lower alkoxy, a second substituent $R_2$ selected from the group consisting of lower alkyl and lower alkoxy, and a third substituent $R_3$ selected from the group consisting of lower alkoxy and halogen.

In other embodiments, $R_3$ is halogen or may be selected from the group consisting of fluorine and chlorine.

In other embodiments, the azo dye further includes at least one sulfonic acid group.

In yet other embodiments $R_3$ is halogen.

In yet other embodiments, $R_1$ is hydroxy and $R_2$ and $R_3$ are both ortho to $R_1$; or $R_1$ is hydroxy and $R_2$ and $R_3$ are methoxy; or $R_1$ is hydroxy and $R_2$ is methyl and $R_3$ is methoxy.

In yet other embodiments R3 is lower alkyl or lower alkoxy.

In still other embodiments, the biodegradable azo dye is selected from the group consisting of 3,5-dimethyl-4-hydroxy-azobenzene-4'-sulfonic acid; 3,5-dimethoxy-4-hydroxy-azobenzene-4'-sulfonic acid; 3,5-difluoro-4-hydroxy-azobenzene-4'-sulfonic acid; 2-hydroxy-4,5-dimethyl-azobenzene-4'-sulfonic acid; and 2-hydroxy-3-methoxy-5-methyl-azobenzene-4'-sulfonic acid.

In yet other embodiments the biodegradable azo dye compound is selected from the group consisting of 3,5-dimethyl-4-hydroxy-azobenzene-4'-sulfonic acid, 3,5-dimethoxy-4-hydroxy-azobenzene-4'-sulfonic acid, and 2-hydroxy-3-methoxy-5-methyl-azobenzene-4'-sulfonic acid.

In other embodiments, the dye compound comprises an azo group having first and second nitrogen atoms linked to first and second aromatic rings, an azo group having a nitrogen atom linked to an aromatic ring, the aromatic ring having a hydroxy group, and two methoxy groups attached thereto. In preferred embodiments, the methoxy groups are both ortho to the hydroxy group.

In other embodiments the compound comprises an azo group having first and second nitrogen atoms linked to first and second aromatic rings, an azo group having a nitrogen atom linked to an aromatic ring, wherein the aromatic ring has a hydroxy group, a methyl group, and a methoxy group attached thereto. Preferably the methyl and methoxy groups are both ortho to the hydroxy group.

In some embodiments the biodegradable dye includes an azo group having first and second nitrogen atoms linked to first and second aromatic rings, an azo group having a nitrogen atom linked to an aromatic ring wherein the aromatic ring has a first substituent R1 selected from the group consisting of hydroxy and lower alkoxy, a second substituent $R_2$ selected from the group consisting of lower alkyl, lower alkoxy and fluorine, and a lower alkoxy substituent $R_3$. In preferred embodiments $R_1$ is hydroxy and $R_2$ is lower alkyl, with $R_2$ and $R_3$ both ortho to $R_1$.

In other embodiments the azo group has first and second nitrogen atoms linked to first and second aromatic rings, with the first aromatic ring having a hydroxy substituent para to the azo group, and a lower alkyl substituent ortho to the hydroxy substituent. In preferred embodiments, the lower alkyl substituent is methyl.

In another embodiment, the azo group has a nitrogen atom linked to an aromatic ring, with the ring having a first substituent $R_1$ and a second substituent $R_2$, wherein both $R_1$ and $R_2$ are lower alkoxy. Preferably, $R_1$ and $R_2$ are both methoxy. In other embodiments $R_1$ and $R_2$ are ortho to each other, or $R_1$ is para to the azo group.

In another embodiment, a plurality of azo groups have nitrogen atoms linked to first, second and third aromatic rings such that the compound of the fully conjugated system, wherein the first aromatic ring has a hydroxy and a lower alkoxy group attached thereto. The lower alkoxy group is preferably a methoxy.

In yet another embodiment, the azo group has first and second nitrogen atoms linked to first and second aromatic rings, wherein the first aromatic ring has a first substituent $R_1$ para to the nitrogen atom, wherein $R_1$ is selected from the group consisting of hydroxy and lower alkoxy, and a second substituent $R_2$ selected from the group consisting of methyl, ethyl and fluorine. In particular embodiments, $R_2$ is ortho to $R_1$. In yet other embodiments $R_2$ is methyl. In another embodiment the first aromatic ring has a third substituent $R_3$ selected from the group consisting of lower alkyl, lower alkoxy and a halogen, particularly wherein $R_3$ is ortho to $R_1$. In some specific embodiments, $R_2$ and $R_3$ are both methyl.

Several especially preferred embodiments are very completely degraded by Phanerochaete, and include 4-dimethylamino-azobenzene-4'-sulfonic acid, 3-methyl-4-hydroxy-azobenzene-4'-sulfonic acid, 3-methoxy-4-hydroxy-azobenzene-4'-sulfonic acid, 3-chloro-4-hydroxy-azobenzene-4'-sulfonic acid, 3-sec-butyl-4-hydroxy-azobenzene-4'-sulfonic acid, 3,5-dimethoxy-4-hydroxy-azobenzene-4'-sulfonic acid, 3,5-difluoro-4-hydroxyazobenzene-4'-sulfonic acid, 2-hydroxy-4,5-dimethyl-azobenzene-4'-sulfonic acid, 2-hydroxy-3-methoxy-5-methyl-azobenzene-4'-sulfonic acid.

Other compounds show some biodegradability when cultured with the Streptomyces strains of the present invention. Examples of such compounds having a higher degree of biodegradation with Streptomyces are the following: 3-methyl-4-hydroxy-azobenzene-4'-sulfonic acid, 3-methoxy-4-hydroxy-azobenzene-4'-sulfonic acid, 3-chloro-4-hydroxy-azobenzene-4'-sulfonic acid, 3-sec-butyl-4-hydroxy-azobenzene-4'-sulfonic acid, 3,5-dimethyl-4-hydroxy-azobenzene-4'-sulfonic acid, 3,5-dimethoxy-4-hydroxy-azobenzene-4'-sulfonic acid, and 2-hydroxy-3-methoxy-5-methyl-azobenzene-4'-sulfonic acid and 4-diethylamino-azobenzene-4'-sulfonic acid.

Especially well degraded dyes with Streptomyces include 3-methyl-4-hydroxy-azobenene-4'-sulfonic acid, 3-methoxy-4-hydroxy-azobenzene-4'-sulfonic acid, 3-sec-butyl-4-hydroxy-azobenzene-4'-sulfonic acid, 3,5-dimethyl-4-hydroxy-azobenzene-4'-sulfonic acid, 3,5-dimethoxy-4-hydroxy-azobenzene-4'-sulfonic acid. These dyes were significantly degraded by Streptomyces, that is degraded more than about 10%.

Particularly high Streptomyces degradation is observed when R1 is hydroxy, and R2 and R3 are methyl, particularly when the methyls are both ortho to the hydroxy. Similarly, high Streptomyces degradation is seen when R1 is hydroxy and R2 and R3 are both methoxy, particularly if both R2 and R3 are ortho to R1. Other Streptomyces degradable compounds include those in which R1 is hydroxy, R2 is methyl and R3 is methoxy, especially wherein R2 and R3 are both ortho to R1.

The present invention also includes a biodegradable composition containing an azo dye having a nitrogen atom linked to an aromatic ring with a lignin-like substitution pattern, wherein the composition also includes a microbe capable of degrading the dye. The ring has a first substituent R1 selected from the group consisting of hydroxy, alkoxy and amino, and a second substituent R2 selected from the group consisting of hydrogen, lower alkoxy, lower alkyl and hydrogen. The amino in preferred embodiments is secondary amine.

In particularly preferred embodiments of the composition, the microbe is *Phanerochaete chrysosporium*. Subspecies of the azo dye that are particularly useful in such a composition include those wherein R1 is hydroxy, particularly if R2 is a lower alkoxy, lower alkyl or halogen.

In yet other embodiments of the composition, the microbe is a Streptomyces, for example *S.rochei*, *S.chromofuscus*, *S.diastaticus*, *S.viridosporus*, or *S.badius*. Particularly useful strains of Streptomyces have been found to be *S.rochei* A10, A14, *S.chromofuscus* A11, A20, *S.diastaticus* A12, A13, *S.viridosporus* T7A and *S.badius* 252. Several compounds have been found to be particularly biodegradable in combination with Streptomyces. Such compounds include those in which R1 is hydroxy, particularly when R2 is ortho to the hydroxy. Enhanced biodegradability is also observed when the ring includes a third ring substituent R3 selected from the group consisting of lower alkyl and lower alkoxy. Biodegradability is particularly high when R1 is a hydroxy para to the azo linkage, and R2 is ortho to the hydroxy. In such embodiments, R2 is most preferably a lower alkoxy or lower alkyl.

In yet other embodiments of the invention, the biodegradability of xenobiotic dyes is increased by introducing a lignin-like aromatic ring into a preexisting azo dye.

Persons skilled in the art will recognize that azo dyes, other than those specifically disclosed, are included in the scope of this invention. Other microorganisms are also suitable for use in degrading these azo dyes. Soil microflora in general are a good source of additional microorganisms, which can be tested for biodegradative capacity as described in this specification. The dyes can also be degraded in soil itself, which contains many species of organisms capable of degrading the lignin-like dyes of the present invention.

The present application describes certain strains of soil Streptomyces species which are particularly effective at degrading the disclosed azo dyes. Such natural variability is expected, and is not evidence of any limitation of the method to use with particular strains of bacteria. Any person skilled in the art will be able to select bacteria from soil or elsewhere using the biotransformation assays disclosed herein. Actual selection of individual biodegradative species and strains is not essential because a mixture of soil microflora contains the microorganisms sufficient for azo dye biotransformation.

Table 4 illustrates that higher concentrations of azo dyes are sometimes less effectively degraded by *P. chrysosporium*. Dye 3, for example, becomes more toxic to the organism at 300 ppm, in contrast to concentrations below 300 ppm. Dyes 4 and 5 do not exhibit a similar degree of inhibition. In any case, toxic inhibition is not complete even at 300 ppm in sensitive organisms. Optimum concentrations of substrate are very specific to the substrate and organism of interest, and are subject to the kind of routine optimization known to those skilled in the art.

Having illustrated and described the principles of the invention in several preferred embodiments, it should be apparent to those skilled in the art that the invention can be modified in arrangement and detail without departing from such principles. We claim all modifications coming within the spirit and scope of the following claims.

We claim:

1. A biodegradable composition, comprising:

a biodegradable azo dye including first and second nitrogen atoms bonded together and linked to first and second aromatic rings, wherein the first ring has a first substituent $R_1$ and a second substituent $R_2$, wherein $R_1$ is selected from the group consisting of a hydroxy group in a position meta or para to the nitrogen atom, a lower alkoxy group, and an amino group, and $R_2$ is selected from the group consisting of lower alkyl, lower alkoxy and halogen, the remainder of the substituents on the first aromatic ring being hydrogen; and a microbe capable of producing extracellular peroxidase for degrading said dye.

2. The composition of claim 1 wherein the microbe is a white-rot fungus *Phanerochaete chrysosporium*.

3. The composition of claim 2 wherein $R_1$ is hydroxy.

4. The composition of claim 3 wherein $R_2$ is a lower alkoxy.

5. The composition of claim 3 wherein $R_2$ is a lower alkyl group.

6. The composition of claim 3 wherein $R_2$ is halogen.

7. A biodegradable composition, comprising:

a biodegradable azo dye selected from the group consisting of 4-dimethylamino-azobenzene-4'-sulfonic acid, 4-diethylamino-azobenzene-4'-sulfonic acid, 3-methyl-4-hydroxy-azobenzene-4'-sulfonic acid, 3-methoxy-4-hydroxy-azobenzene-4'-sulfonic acid, 3-chloro-4-hydroxy-azobenzene-4'-sulfonic acid, 3-sec-butyl-4-hydroxy-azobenzene-4'-sulfonic acid, 3,5-dimethoxy-4-hydroxy-azobenzene-4'-sulfonic acid, 3,5-difluoro-4-hydroxy-azobenzene-4'-sulfonic acid, 3,5-dimethyl-4-hydroxy-azobenzene-4'-sulfonic acid, 2-hydroxy-4,5-dimethyl-azobenzene-4'-sulfonic acid, 2-hydroxy-3-methoxy-5-methyl-azobenzene-4'-sulfonic acid, and 4-(3-methoxy-4-hydroxyphenylazo)-azobenzene-3,4'-disulfonic acid; and a microbe capable of producing extracellular peroxidase for degrading said dye.

8. A biodegradable composition comprising:

a biodegradable azo dye having first and second nitrogen atoms bonded together and linked to first and second aromatic rings, wherein the first ring has a first substituent $R_1$ and a second substituent $R_2$, wherein $R_1$ is selected from the group consisting of hydroxy, lower alkoxy, amino, and $R_2$ is selected from the group consisting of hydrogen, lower alkyl, lower alkoxy and halogen, the concentration of the azo dye being less than about 150 ppm; and a microbe capable of producing extracellular peroxidase for degrading said dye.

9. The composition according to claim 1 wherein the microbe is *Phanerochaete chrysosporium* and the azo dye is selected from the group consisting of 4-dimethylamino-azobenzene-4'-sulfonic acid, 4-diethylamino-azobenzene-4'sulfonic acid, 3-methyl-4-hydroxy-azobenzene-4'-sulfonic acid, 3-methoxy-4-hydroxy-azobenzene-4'-sulfonic acid, 3-chloro-4-hydroxy-azobenzene-4'-sulfonic acid, 3-sec-butyl-4-hydroxy-azobenzene-4'-sulfonic acid, 3,5-dimethoxy-4-hydroxy-azobenzene-4'-sulfonic acid, 3,5-difluoro-4-hydroxy-azobenzene-4-sulfonic acid, 3,5-dimethyl-4-hydroxy-azobenzene-4'-sulfonic acid, 2-hydroxy-4,5-dimethyl-azobenzene-4'-sulfonic acid, 2-hydroxy-3-methoxy-5-methyl-azobenzene-4'-sulfonic acid, 4-(3-methoxy-4-hydroxyphenylazo)-azobenzene-3,4,-disulfonic acid, 2-hydroxy-5-ethyl-azobenzene-4'-sulfonic acid, 3,4-dimethoxy-azobenzene-4'-sulfonic acid, 1-(4'-benzenesulfoncic acid)-4-hydroxynaphthalene, 4-methoxy-azobenzene-4'-sulfonic acid, 4-amino-1,1'-azobenzene-3,4'-disulfonic acid, 4-aminoazobenzene-4'-sulfonic acid and 4-hydroxy-azobenzene-4'-sulfonic acid.

10. A biodegradable composition, comprising:

a biodegradable azo dye selected from the group consisting of 3-methyl-4-hydroxy-azobenzene-4'-sulfonic acid, 3-methoxy-4-hydroxy-azobenzene-4'-sulfonic acid, 3-sec-butyl-4-hydroxy-azobenzene-4'-sulfonic acid, 3,5-dimethoxy-4-hydroxy-azobenzene-4'-sulfonic acid, 3,5-dimethyl-4-hydroxy-azobenzene-4'-sulfonic acid, 2-hydroxy-4,5-dimethyl-azobenzene-4'-sulfonic acid, 2-hydroxy-3-methoxy-5-methyl-azobenzene-4'-sulfonic acid, 4-(3-methoxy-4-hydroxyphenylazo)-azobenzene-3,4'-disulfonic acid, 2-hydroxy-5-ethyl-azobenzene-4'-sulfonic acid, 3,4-dimethoxy-azobenzene-4'-sulfonic acid, and 1-(4'-benzenesulfoncic acid)-4-hydroxynaphthalene; and a microbe capable of producing extracellular peroxidase for degrading said dye.

11. A biodegradable composition, comprising:

a biodegradable azo dye including first and second nitrogen atoms bonded together and linked to first and second aromatic rings, wherein the first ring has a first substituent selected from the group consisting of hydroxy and lower alkoxy and a second electron-releasing group $R_2$; and a microbe capable of producing extracellular peroxidase for degrading said dye.

12. The composition of claim 11 wherein the microbe is a Streptomyces, $R_1$ is hydroxy and $R_2$ is selected from the group consisting of lower alkyl and lower alkoxy.

13. The composition according to claim 12 wherein the azo dye is selected from the group consisting of 4-(3-methoxy-4-hydroxyphenylazo)-azobenzene-3,4'-disulfonic acid, 3-methoxy-4-hydroxy-azobenzene-4'-sulfonic acid, and 2-hydroxy-5-ethyl-azobenzene-4'-sulfonic acid.

14. The composition of claim 12 wherein $R_1$ is para to the azo group.

15. The composition of claim 14 wherein $R_2$ is ortho to $R_1$.

16. A biodegradable composition, comprising:

a biodegradable azo dye including first and second nitrogen atoms bonded together and linked to first and second aromatic rings, wherein the first ring has a first hydroxy substituent $R_1$ and a second substituent $R_2$ which is selected from the group consisting of lower alkyl and lower alkoxy, and wherein the dye further comprises a third ring substituent $R_3$ selected from the group consisting of lower alkyl and lower alkoxy; and a Streptomyces capable of producing extracellular peroxidase for degrading said dye.

17. The composition according to claim 15 wherein both $R_2$ and $R_3$ are ortho to $R_1$.

18. The composition according to claim 16 wherein the azo dye is selected from the group consisting of 3,5-dimethyl-4-hydroxy-azobenzene-4'-sulfonic acid and 3,5-dimethoxy-4-hydroxy-azobenzene-4'-sulfonic acid.

19. The composition of claim 11 wherein the Streptomyces is selected from the group consisting of *S.rochei, S.badius, S.chromofuscus,* and *S.diastaticus.*

20. The composition of claim 12 wherein $R_2$ is a lower alkoxy.

21. The composition of claim 12 wherein $R_2$ is a lower alkyl group.

22. A biodegradable composition comprising:

a biodegradable azo dye having first and second nitrogen atoms bonded together and linked to first and second aromatic rings, wherein the first ring is a naphthyl ring and has a first substituent $R_1$ selected from the group consisting of hydroxy, lower alkoxy and amino, and a second substituent $R_2$ selected from the group consisting of hydrogen, lower alkyl, lower alkoxy and halogen; and a microbe capable of producing extracellular peroxidase for degrading said dye.

23. The composition according to claim 22 wherein the azo dye is selected from the group consisting of 1-phenylazo-2-hydroxynaphthalene-6-sulfonic acid and and 4-(4-hydroxynaphthylazo)-benzenesulfonic acid.

24. The composition according to claim 22 wherein the hydroxy group is para to the azo group.

25. The composition of claim 12 wherein the Streptomyces is capable of degrading vanillic acid.

26. A biodegradable composition comprising:

a biodegradable azo dye having first and second nitrogen atoms bonded together and linked to first and second aromatic rings, wherein the first ring has a first substituent $R_1$ selected from the group consisting of hydroxy, lower alkoxy and amino, and a second substituent $R_2$ selected from the group consisting of hydrogen, lower alkyl, lower alkoxy and halogen; and a soil microflora.

27. The composition according to claim 1 wherein the composition further includes an amount of veratryl alcohol effective to recycle lignin peroxidase II as the dye is degraded.

* * * * *